(12) United States Patent
Miyata

(10) Patent No.: US 7,026,126 B1
(45) Date of Patent: Apr. 11, 2006

(54) METHOD FOR DETECTING MEGSIN PROTEIN AND USE THEREOF

(75) Inventor: Toshio Miyata, 102 Ekuseru Isehara, 16-25, Sakuradai 2-chome, Isehara-shi, Kanagawa 259-1132 (JP)

(73) Assignees: Kiyoshi Kurekawa, Tokyo (JP); Toshio Miyata, Kanagawa (JP); Tokai University Educational System, Osaka (JP); Fuso Pharmaceutical Industries, Ltd., Tokyo (JP)

(*) Notice: Subject to any disclaimer, the term of this patent is extended or adjusted under 35 U.S.C. 154(b) by 0 days.

(21) Appl. No.: 09/936,883

(22) PCT Filed: Mar. 17, 2000

(86) PCT No.: PCT/JP00/01646

§ 371 (c)(1),
(2), (4) Date: Dec. 21, 2001

(87) PCT Pub. No.: WO00/57189

PCT Pub. Date: Sep. 28, 2000

(30) Foreign Application Priority Data

| Mar. 19, 1999 | (JP) | ................................. 11-075305 |
| Oct. 28, 1999 | (JP) | ................................. 11-306623 |

(51) Int. Cl.
*G01N 33/53* (2006.01)
(52) U.S. Cl. ........................ 435/7.1; 435/7.92; 435/975; 436/501; 436/518; 436/808; 436/811
(58) Field of Classification Search ................ 435/7.1, 435/7.12, 7.13, 7.94, 925, 7.92, 7.93, 975; 436/518, 524, 525, 526, 808; 530/300, 350
See application file for complete search history.

(56) References Cited

U.S. PATENT DOCUMENTS 5,445,970 A * 8/1995 Rohr .......................... 436/526
5,831,030 A * 11/1998 Tsujimoto et al. ....... 530/387.9
6,297,062 B1 * 10/2001 Gombinski ................. 436/526

FOREIGN PATENT DOCUMENTS

| CN | 1030139 A | 1/1989 |
| EP | 1 018 551 A1 | 7/2000 |
| WO | WO 87/07386 | 12/1987 |
| WO | WO 99/15652 | 4/1999 |

OTHER PUBLICATIONS

Tsujimoto et al., Purification, cDNA Cloning, and Characterization of a New Serpin with Megakaryocyte Maturation Activity, Journal of Biological chemistry, vol. 272, No. 24, 15373-15380, 1997.*

Miyata et al., "Transcriptional Regulation of a Mesangium-Predonminant Gene, Megsin" *J., Am. Soc. Nep.* 9.503A (1997) (Abstract).

Miyata et al., "A Mesangium-predominant Gene, Megsin, Is a New Serpin Upregulated in IgA Nephropathy" *J. Clin. Invest.* 120(4):828-836 (1998).

Yang, J., et al., "Preparation and characterization of Anti-Idiotype Monlonal Antibodies Bearing The Internal Image of Nasopharyngeal Cancer Associated Antigen" *Labeled Immunoassays and Clinical Medicine*, 1(2):79-83 (1994).

Nangaku et al., "A New Mesangium-Predominant Gene, Megsin, Is Upregulated In The Mesangioproliferative Nephritis Model of Rats" *Journal of American Society of Nephrology*, Williams and Wilkins, Baltimore, MD 9:505A (Sep. 1998) (Abstract).

Suzuki et al., "Expression of Megsin mRNA, a Novel Mesangium-Predominant Gene, in the Renal Tissues of Various Glomerular Diseases" *J. Am Soc Nephrol*, 10:2606-2613 (1999).

* cited by examiner

*Primary Examiner*—Long V. Le
*Assistant Examiner*—Gary W. Counts
(74) *Attorney, Agent, or Firm*—Karl Bozicevic; Bozicevic, Field & Francis LLP

(57) ABSTRACT

The present invention provides a method for evaluating renal functions by measuring megsin protein in a biological specimen. Moreover, the present invention provides immunological assay reagents, as well as kits useful for the measurement of megsin protein in the biological specimen.

10 Claims, 13 Drawing Sheets

SEQUENCE LISTING

```
<160> NUMBER OF SEQ ID NOS: 21

<210> SEQ ID NO 1
<211> LENGTH: 1143
<212> TYPE: DNA
<213> ORGANISM: Homo sapiens
<220> FEATURE:
<221> NAME/KEY: CDS
<222> LOCATION: (1)..(1140)
<300> PUBLICATION INFORMATION:
<302> TITLE: A mesangium-predominant gene, megsin, is a new serpin
      upregulated in IgA nephropathy.
<303> JOURNAL: J. Clin. Invest.
<304> VOLUME: 120
<305> ISSUE: 4
<306> PAGES: 828-836
<307> DATE: 1998-08-15

<400> SEQUENCE: 1 atg gcc tcc ctt gct gca gca aat gca gag ttt tgc ttc aac ctg ttc      48
Met Ala Ser Leu Ala Ala Ala Asn Ala Glu Phe Cys Phe Asn Leu Phe
 1               5                  10                  15 aga gag atg gat gac aat caa gga aat gga aat gtg ttc ttt tcc tct      96
Arg Glu Met Asp Asp Asn Gln Gly Asn Gly Asn Val Phe Phe Ser Ser
            20                  25                  30 ctg agc ctc ttc gct gcc ctg gcc ctg gtc cgc ttg ggc gct caa gat     144
Leu Ser Leu Phe Ala Ala Leu Ala Leu Val Arg Leu Gly Ala Gln Asp
        35                  40                  45 gac tcc ctc tct cag att gat aag ttg ctt cat gtt aac act gcc tca     192
Asp Ser Leu Ser Gln Ile Asp Lys Leu Leu His Val Asn Thr Ala Ser
    50                  55                  60 gga tat gga aac tct tct aat agt cag tca ggg ctc cag tct caa ctg     240
Gly Tyr Gly Asn Ser Ser Asn Ser Gln Ser Gly Leu Gln Ser Gln Leu
65                  70                  75                  80 aaa aga gtt ttt tct gat ata aat gca tcc cac aag gat tat gat ctc     288
Lys Arg Val Phe Ser Asp Ile Asn Ala Ser His Lys Asp Tyr Asp Leu
                85                  90                  95 agc att gtg aat ggg ctt ttt gct gaa aaa gtg tat ggc ttt cat aag     336
Ser Ile Val Asn Gly Leu Phe Ala Glu Lys Val Tyr Gly Phe His Lys
            100                 105                 110 gac tac att gag tgt gcc gaa aaa tta tac gat gcc aaa gtg gag cga     384
Asp Tyr Ile Glu Cys Ala Glu Lys Leu Tyr Asp Ala Lys Val Glu Arg
        115                 120                 125 gtt gac ttt acg aat cat tta gaa gac act aga cgt aat att aat aag     432
Val Asp Phe Thr Asn His Leu Glu Asp Thr Arg Arg Asn Ile Asn Lys
    130                 135                 140 tgg gtt gaa aat gaa aca cat ggc aaa atc aag aac gtg att ggt gaa     480
```

-continued

```
          Trp Val Glu Asn Glu Thr His Gly Lys Ile Lys Asn Val Ile Gly Glu
          145                 150                 155                 160 ggt ggc ata agc tca tct gct gta atg gtg ctg gtg aat gct gtg tac            528
Gly Gly Ile Ser Ser Ser Ala Val Met Val Leu Val Asn Ala Val Tyr
                165                 170                 175 ttc aaa ggc aag tgg caa tca gcc ttc acc aag agc gaa acc ata aat            576
Phe Lys Gly Lys Trp Gln Ser Ala Phe Thr Lys Ser Glu Thr Ile Asn
            180                 185                 190 tgc cat ttc aaa tct ccc aag tgc tct ggg aag gca gtc gcc atg atg            624
Cys His Phe Lys Ser Pro Lys Cys Ser Gly Lys Ala Val Ala Met Met
        195                 200                 205 cat cag gaa cgg aag ttc aat ttg tct gtt att gag gac cca tca atg            672
His Gln Glu Arg Lys Phe Asn Leu Ser Val Ile Glu Asp Pro Ser Met
    210                 215                 220 aag att ctt gag ctc aga tac aat ggt ggc ata aac atg tac gtt ctg            720
Lys Ile Leu Glu Leu Arg Tyr Asn Gly Gly Ile Asn Met Tyr Val Leu
225                 230                 235                 240 ctg cct gag aat gac ctc tct gaa att gaa aac aaa ctg acc ttt cag            768
Leu Pro Glu Asn Asp Leu Ser Glu Ile Glu Asn Lys Leu Thr Phe Gln
                245                 250                 255 aat cta atg gaa tgg acc aat cca agg cga atg acc tct aag tat gtt            816
Asn Leu Met Glu Trp Thr Asn Pro Arg Arg Met Thr Ser Lys Tyr Val
            260                 265                 270 gag gta ttt ttt cct cag ttc aag ata gag aag aat tat gaa atg aaa            864
Glu Val Phe Phe Pro Gln Phe Lys Ile Glu Lys Asn Tyr Glu Met Lys
        275                 280                 285 caa tat ttg aga gcc cta ggg ctg aaa gat atc ttt gat gaa tcc aaa            912
Gln Tyr Leu Arg Ala Leu Gly Leu Lys Asp Ile Phe Asp Glu Ser Lys
    290                 295                 300 gca gat ctc tct ggg att gct tcg ggg ggt cgt ctg tat ata tca agg            960
Ala Asp Leu Ser Gly Ile Ala Ser Gly Gly Arg Leu Tyr Ile Ser Arg
305                 310                 315                 320 atg atg cac aaa tct tac ata gag gtc act gag gag ggc acc gag gct           1008
Met Met His Lys Ser Tyr Ile Glu Val Thr Glu Glu Gly Thr Glu Ala
                325                 330                 335 act gct gcc aca gga agt aat att gta gaa aag caa ctc cct cag tcc           1056
Thr Ala Ala Thr Gly Ser Asn Ile Val Glu Lys Gln Leu Pro Gln Ser
            340                 345                 350 acg ctg ttt aga gct gac cac cca ttc cta ttt gtt atc agg aag gat           1104
Thr Leu Phe Arg Ala Asp His Pro Phe Leu Phe Val Ile Arg Lys Asp
        355                 360                 365 gac atc atc tta ttc agt ggc aaa gtt tct tgc cct tga                       1143
Asp Ile Ile Leu Phe Ser Gly Lys Val Ser Cys Pro
    370                 375                 380

<210> SEQ ID NO 2
<211> LENGTH: 380
<212> TYPE: PRT
<213> ORGANISM: Homo sapiens

<400> SEQUENCE: 2

Met Ala Ser Leu Ala Ala Ala Asn Ala Glu Phe Cys Phe Asn Leu Phe
1               5                   10                  15

Arg Glu Met Asp Asp Asn Gln Gly Asn Gly Asn Val Phe Phe Ser Ser
            20                  25                  30

Leu Ser Leu Phe Ala Ala Leu Ala Leu Val Arg Leu Gly Ala Gln Asp
        35                  40                  45

Asp Ser Leu Ser Gln Ile Asp Lys Leu Leu His Val Asn Thr Ala Ser
    50                  55                  60
```

```
Gly Tyr Gly Asn Ser Ser Asn Ser Gln Ser Gly Leu Gln Ser Gln Leu
 65                  70                  75                  80

Lys Arg Val Phe Ser Asp Ile Asn Ala Ser His Lys Asp Tyr Asp Leu
                 85                  90                  95

Ser Ile Val Asn Gly Leu Phe Ala Glu Lys Val Tyr Gly Phe His Lys
            100                 105                 110

Asp Tyr Ile Glu Cys Ala Glu Lys Leu Tyr Asp Ala Lys Val Glu Arg
        115                 120                 125

Val Asp Phe Thr Asn His Leu Glu Asp Thr Arg Arg Asn Ile Asn Lys
    130                 135                 140

Trp Val Glu Asn Glu Thr His Gly Lys Ile Lys Asn Val Ile Gly Glu
145                 150                 155                 160

Gly Gly Ile Ser Ser Ser Ala Val Met Val Leu Val Asn Ala Val Tyr
                165                 170                 175

Phe Lys Gly Lys Trp Gln Ser Ala Phe Thr Lys Ser Glu Thr Ile Asn
            180                 185                 190

Cys His Phe Lys Ser Pro Lys Cys Ser Gly Lys Ala Val Ala Met Met
        195                 200                 205

His Gln Glu Arg Lys Phe Asn Leu Ser Val Ile Glu Asp Pro Ser Met
    210                 215                 220

Lys Ile Leu Glu Leu Arg Tyr Asn Gly Gly Ile Asn Met Tyr Val Leu
225                 230                 235                 240

Leu Pro Glu Asn Asp Leu Ser Glu Ile Glu Asn Lys Leu Thr Phe Gln
                245                 250                 255

Asn Leu Met Glu Trp Thr Asn Pro Arg Arg Met Thr Ser Lys Tyr Val
            260                 265                 270

Glu Val Phe Phe Pro Gln Phe Lys Ile Glu Lys Asn Tyr Glu Met Lys
        275                 280                 285

Gln Tyr Leu Arg Ala Leu Gly Leu Lys Asp Ile Phe Asp Glu Ser Lys
    290                 295                 300

Ala Asp Leu Ser Gly Ile Ala Ser Gly Gly Arg Leu Tyr Ile Ser Arg
305                 310                 315                 320

Met Met His Lys Ser Tyr Ile Glu Val Thr Glu Glu Gly Thr Glu Ala
                325                 330                 335

Thr Ala Ala Thr Gly Ser Asn Ile Val Glu Lys Gln Leu Pro Gln Ser
            340                 345                 350

Thr Leu Phe Arg Ala Asp His Pro Phe Leu Phe Val Ile Arg Lys Asp
        355                 360                 365

Asp Ile Ile Leu Phe Ser Gly Lys Val Ser Cys Pro
    370                 375                 380

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:Artificially
      synthesized degenerative primer sequence
<220> FEATURE:
<221> NAME/KEY: misc_feature
<222> LOCATION: 26, 29
<223> OTHER INFORMATION: n is a or g or c or t.

<400> SEQUENCE: 3
gtgaatgctg tgtacttaaa ggcaantgn                                    29

<210> SEQ ID NO 4
```

```
<211> LENGTH: 17
<212> TYPE: DNA
<213> ORGANISM: Artificial Sequence
<220> FEATURE:
<223> OTHER INFORMATION: Description of Artificial Sequence:Artificially
      synthesized degenerative primer sequence
<220> FEATURE:
<221> NAME/KEY: misc_feature
<222> LOCATION: 3, 9, 15
<223> OTHER INFORMATION: n is a or g or c or t.

<400> SEQUENCE: 4
aanagraang grtcngc                                                    17

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Artificially
      synthesized degenerative primer sequence
<220> FEATURE:
<221> NAME/KEY: misc_feature
<222> LOCATION: 6, 9, 12, 15, 18, 21
<223> OTHER INFORMATION: n is a or g or c or t.

<400> SEQUENCE: 5
atggcntcng cngcngcngc naaygc                                          26

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence:Artificially
      synthesized degenerative primer sequence

<400> SEQUENCE: 6
cgacctccag aggcaattcc agagagatca gccctgg                              37

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:Artificially
      synthesized degenerative primer sequence

<400> SEQUENCE: 7
gtcttccaag cctacagatt tcaagtggct cctc                                 34

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Artificially
      synthesized antisense primer sequence

<400> SEQUENCE: 8
gctcagggca gtgaagatgc tcagggaaga                                      30

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:Artificially
      synthesized antisense primer sequence
```

```
<400> SEQUENCE: 9
ctgacgtgca cagtcacctc gagcacc                                          27

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:Artificially
      synthesized sense primer sequence

<400> SEQUENCE: 10
gaggtctcag aagaaggcac tgaggcaact gctgcc                                36

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence:Artificially
      synthesized domain peptide of human megsin

<400> SEQUENCE: 11

Phe Arg Glu Met Asp Asp Asn Gln Gly Asn Gly Asn Val Phe Phe
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence:Artificially
      synthesized domain peptide of human megsin

<400> SEQUENCE: 12

Ser Gln Ser Gly Leu Gln Ser Gln Leu Lys Arg Val Phe Ser Asp
 1               5                  10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence:Artificially
      synthesized domain peptide of human megsin

<400> SEQUENCE: 13

Ala Thr Gly Ser Asn Ile Val Glu Lys Gln Leu Pro Gln Ser Thr Leu
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence:Artificially
      synthesized domain peptide of human megsin

<400> SEQUENCE: 14

Asn Leu Met Glu Trp Thr Asn Pro Arg Arg Met Thr Ser Lys Tyr Val
 1               5                  10                  15

<210> SEQ ID NO 15
<211> LENGTH: 15
<212> TYPE: PRT
<213> ORGANISM: Artificial Sequence
```

```
<220> FEATURE:
<223> OTHER INFORMATION: Description of Artificial Sequence:Artificially
      synthesized domain peptide of human megsin

<400> SEQUENCE: 15

Ser Asn Ile Val Glu Lys Gln Leu Pro Gln Ser Thr Leu Phe Arg
  1               5                  10                  15

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence:Artificially
      synthesized domain peptide of human megsin

<400> SEQUENCE: 16

Leu Gly Leu Gln Tyr Gln Leu Lys Arg Val Leu Ala Asp
  1               5                  10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence:Artificially
      synthesized domain peptide of human megsin

<400> SEQUENCE: 17

Glu Ser Asn Ile Val Glu Lys Leu Leu Pro Glu Ser Thr Val
  1               5                  10

<210> SEQ ID NO 18
<211> LENGTH: 1229
<212> TYPE: DNA
<213> ORGANISM: Rattus norvegicus
<220> FEATURE:
<221> NAME/KEY: CDS
<222> LOCATION: (8)..(1147)
<220> FEATURE:
<221> NAME/KEY: misc_feature
<222> LOCATION: 158, 159, 160, 287, 288, 289
<223> OTHER INFORMATION: n is a or g or c or t.
<300> PUBLICATION INFORMATION:
<310> PATENT DOCUMENT NUMBER: PCT/JP98/04269
<311> PATENT FILING DATE: 1998-09-22

<400> SEQUENCE: 18 tttcaaa atg gcc tcc ctt gct gca gca aat gca gaa ttt ggc ttc gac        49
        Met Ala Ser Leu Ala Ala Ala Asn Ala Glu Phe Gly Phe Asp
          1               5                  10 tta ttc aga gag atg gat agt agt caa gga aac gga aat gta ttc ttc        97
Leu Phe Arg Glu Met Asp Ser Ser Gln Gly Asn Gly Asn Val Phe Phe
 15                  20                  25                  30 tct tcc ctg agc atc ttc act gcc ctg agc cta atc cgt ttg ggt gct       145
Ser Ser Leu Ser Ile Phe Thr Ala Leu Ser Leu Ile Arg Leu Gly Ala
                 35                  40                  45 cga ggt gac tgt nnn cgt cag att gac aag gcc ctg cac ttt atc tcc       193
Arg Gly Asp Cys Xaa Arg Gln Ile Asp Lys Ala Leu His Phe Ile Ser
             50                  55                  60 cca tca aga caa ggg aat tca tcg aac agt cag cta gga ctg caa tat       241
Pro Ser Arg Gln Gly Asn Ser Ser Asn Ser Gln Leu Gly Leu Gln Tyr
         65                  70                  75 caa ttg aaa aga gtt ctt gct gac ata aac tca tct cat aag gat nnn       289
Gln Leu Lys Arg Val Leu Ala Asp Ile Asn Ser Ser His Lys Asp Xaa
     80                  85                  90
```

| | | |
|---|---|---|
| aaa ctc agc att gcc aat gga gtt ttt gca gag aaa gta ttt gat ttt<br>Lys Leu Ser Ile Ala Asn Gly Val Phe Ala Glu Lys Val Phe Asp Phe<br>95                         100                    105                      110 | 337 |
| cat aag agc tat atg gag tgt gct gaa aac tta tac aat gct aaa gtg<br>His Lys Ser Tyr Met Glu Cys Ala Glu Asn Leu Tyr Asn Ala Lys Val<br>                115                    120                    125 | 385 |
| gaa aga gtt gat ttt aca aat gat ata caa gaa acc aga ttt aaa att<br>Glu Arg Val Asp Phe Thr Asn Asp Ile Gln Glu Thr Arg Phe Lys Ile<br>          130                    135                    140 | 433 |
| aat aaa tgg att gaa aat gaa aca cat ggc aaa atc aag aag gtg ttg<br>Asn Lys Trp Ile Glu Asn Glu Thr His Gly Lys Ile Lys Lys Val Leu<br>               145                    150                    155 | 481 |
| ggg gac agc agc ctc agc tca tca gct gtc atg gtg cta gtg aat gct<br>Gly Asp Ser Ser Leu Ser Ser Ser Ala Val Met Val Leu Val Asn Ala<br>160                         165                    170 | 529 |
| gtt tac ttc aaa ggc aag tgg aaa tcg gcc ttc acc aag agt gat acc<br>Val Tyr Phe Lys Gly Lys Trp Lys Ser Ala Phe Thr Lys Ser Asp Thr<br>175                       180                    185                    190 | 577 |
| ctc agt tgc cat ttc agg tct ccc agc ggt cct gga aaa gca gtt aat<br>Leu Ser Cys His Phe Arg Ser Pro Ser Gly Pro Gly Lys Ala Val Asn<br>                    195                    200                    205 | 625 |
| atg atg cat caa gaa cgg agg ttc aat ttg tct acc att cag gag cca<br>Met Met His Gln Glu Arg Arg Phe Asn Leu Ser Thr Ile Gln Glu Pro<br>          210                    215                    220 | 673 |
| cca atg cag att ctt gag cta caa tat cat ggt ggc ata agc atg tac<br>Pro Met Gln Ile Leu Glu Leu Gln Tyr His Gly Gly Ile Ser Met Tyr<br>               225                    230                    235 | 721 |
| atc atg ttg ccc gag gat gac cta tcc gaa att gaa agc aag ctg agt<br>Ile Met Leu Pro Glu Asp Asp Leu Ser Glu Ile Glu Ser Lys Leu Ser<br>240                       245                    250 | 769 |
| ttc cag aat cta atg gac tgg aca aat agc agg aag atg aaa tct cag<br>Phe Gln Asn Leu Met Asp Trp Thr Asn Ser Arg Lys Met Lys Ser Gln<br>255                       260                    265                    270 | 817 |
| tat gtg aat gtg ttt ctc ccc cag ttc aag ata gag aaa gat tat gaa<br>Tyr Val Asn Val Phe Leu Pro Gln Phe Lys Ile Glu Lys Asp Tyr Glu<br>                    275                    280                    285 | 865 |
| atg agg agc cac ttg aaa tct gta ggc ttg gaa gac atc ttt gtt gag<br>Met Arg Ser His Leu Lys Ser Val Gly Leu Glu Asp Ile Phe Val Glu<br>          290                    295                    300 | 913 |
| tcc agg gct gat ctg tct gga att gcc tct gga ggt cgt ctc tat gta<br>Ser Arg Ala Asp Leu Ser Gly Ile Ala Ser Gly Gly Arg Leu Tyr Val<br>               305                    310                    315 | 961 |
| tca aag cta atg cac aag tcc ctc ata gag gtc tca gaa gaa ggc acc<br>Ser Lys Leu Met His Lys Ser Leu Ile Glu Val Ser Glu Glu Gly Thr<br>320                       325                    330 | 1009 |
| gag gca act gct gcc aca gaa agt aac atc gtt gaa aag cta ctt cct<br>Glu Ala Thr Ala Ala Thr Glu Ser Asn Ile Val Glu Lys Leu Leu Pro<br>335                       340                    345                    350 | 1057 |
| gaa tcc acg gtg ttc aga gct gac cgc ccc ttt ctg ttt gtc att agg<br>Glu Ser Thr Val Phe Arg Ala Asp Arg Pro Phe Leu Phe Val Ile Arg<br>                    355                    360                    365 | 1105 |
| aag aat ggc atc atc tta ttt act ggc aaa gtc tcg tgt cct<br>Lys Asn Gly Ile Ile Leu Phe Thr Gly Lys Val Ser Cys Pro<br>370                       375                    380 | 1147 |
| tgaaattcta tttggttttc catacactaa caggcatgaa gaaacatcat aagtgaatag | 1207 |
| aattgtaatt ggaagtacat gg | 1229 |

<210> SEQ ID NO 19
<211> LENGTH: 380

-continued

```
<212> TYPE: PRT
<213> ORGANISM: Rattus norvegicus
<220> FEATURE:
<221> NAME/KEY: misc_feature
<222> LOCATION: 51, 94
<223> OTHER INFORMATION: Xaa is unknown.

<400> SEQUENCE: 19
```

Met Ala Ser Leu Ala Ala Asn Ala Glu Phe Gly Phe Asp Leu Phe
 1               5                  10                  15

Arg Glu Met Asp Ser Ser Gln Gly Asn Gly Asn Val Phe Phe Ser Ser
             20                  25                  30

Leu Ser Ile Phe Thr Ala Leu Ser Leu Ile Arg Leu Gly Ala Arg Gly
             35                  40                  45

Asp Cys Xaa Arg Gln Ile Asp Lys Ala Leu His Phe Ile Ser Pro Ser
         50                  55                  60

Arg Gln Gly Asn Ser Ser Asn Ser Gln Leu Gly Leu Gln Tyr Gln Leu
 65                  70                  75                  80

Lys Arg Val Leu Ala Asp Ile Asn Ser Ser His Lys Asp Xaa Lys Leu
                 85                  90                  95

Ser Ile Ala Asn Gly Val Phe Ala Glu Lys Val Phe Asp Phe His Lys
            100                 105                 110

Ser Tyr Met Glu Cys Ala Glu Asn Leu Tyr Asn Ala Lys Val Glu Arg
        115                 120                 125

Val Asp Phe Thr Asn Asp Ile Gln Glu Thr Arg Phe Lys Ile Asn Lys
130                 135                 140

Trp Ile Glu Asn Glu Thr His Gly Lys Ile Lys Lys Val Leu Gly Asp
145                 150                 155                 160

Ser Ser Leu Ser Ser Ser Ala Val Met Val Leu Val Asn Ala Val Tyr
                165                 170                 175

Phe Lys Gly Lys Trp Lys Ser Ala Phe Thr Lys Ser Asp Thr Leu Ser
            180                 185                 190

Cys His Phe Arg Ser Pro Ser Gly Pro Gly Lys Ala Val Asn Met Met
        195                 200                 205

His Gln Glu Arg Arg Phe Asn Leu Ser Thr Ile Gln Glu Pro Pro Met
    210                 215                 220

Gln Ile Leu Glu Leu Gln Tyr His Gly Gly Ile Ser Met Tyr Ile Met
225                 230                 235                 240

Leu Pro Glu Asp Asp Leu Ser Glu Ile Glu Ser Lys Leu Ser Phe Gln
                245                 250                 255

Asn Leu Met Asp Trp Thr Asn Ser Arg Lys Met Lys Ser Gln Tyr Val
            260                 265                 270

Asn Val Phe Leu Pro Gln Phe Lys Ile Glu Lys Asp Tyr Glu Met Arg
        275                 280                 285

Ser His Leu Lys Ser Val Gly Leu Glu Asp Ile Phe Val Glu Ser Arg
    290                 295                 300

Ala Asp Leu Ser Gly Ile Ala Ser Gly Gly Arg Leu Tyr Val Ser Lys
305                 310                 315                 320

Leu Met His Lys Ser Leu Ile Glu Val Ser Glu Glu Gly Thr Glu Ala
                325                 330                 335

Thr Ala Ala Thr Glu Ser Asn Ile Val Glu Lys Leu Leu Pro Glu Ser
            340                 345                 350

Thr Val Phe Arg Ala Asp Arg Pro Phe Leu Phe Val Ile Arg Lys Asn
        355                 360                 365

Gly Ile Ile Leu Phe Thr Gly Lys Val Ser Cys Pro

-continued

```
<210> SEQ ID NO 20
<211> LENGTH: 1147
<212> TYPE: DNA
<213> ORGANISM: Mus musculus
<220> FEATURE:
<221> NAME/KEY: CDS
<222> LOCATION: (1)..(1104)
<300> PUBLICATION INFORMATION:
<310> PATENT DOCUMENT NUMBER: PCT/JP98/04269
<311> PATENT FILING DATE: 1998-09-22

<400> SEQUENCE: 20 ttc gac tta ttc aga gag atg gat agt agc caa gga aat gga aat gta         48
Phe Asp Leu Phe Arg Glu Met Asp Ser Ser Gln Gly Asn Gly Asn Val
 1               5                  10                  15 ttc ttc tct tcc ctg agc atc ttc act gcc ctg acc cta atc cgt ctg         96
Phe Phe Ser Ser Leu Ser Ile Phe Thr Ala Leu Thr Leu Ile Arg Leu
                20                  25                  30 ggt gct cga ggt gac tgt gca cgt cag att gac aag gca ctg cac ttt        144
Gly Ala Arg Gly Asp Cys Ala Arg Gln Ile Asp Lys Ala Leu His Phe
            35                  40                  45 aac ata cca tca aga caa gga aac tca tct aat aat cag cca gga ctt        192
Asn Ile Pro Ser Arg Gln Gly Asn Ser Ser Asn Asn Gln Pro Gly Leu
        50                  55                  60 cag tat caa ttg aaa aga gtt ctt gct gac ata aac tca tct cat aag        240
Gln Tyr Gln Leu Lys Arg Val Leu Ala Asp Ile Asn Ser Ser His Lys
 65                  70                  75                  80 gat tat gaa ctc agc att gcc act gga gtt ttt gca gaa aaa gtc tat        288
Asp Tyr Glu Leu Ser Ile Ala Thr Gly Val Phe Ala Glu Lys Val Tyr
                 85                  90                  95 gac ttt cat aag aac tac att gag tgt gct gaa aac tta tac aat gct        336
Asp Phe His Lys Asn Tyr Ile Glu Cys Ala Glu Asn Leu Tyr Asn Ala
            100                 105                 110 aaa gtg gaa aga gtt gac ttc aca aat gat gta caa gat acc aga ttt        384
Lys Val Glu Arg Val Asp Phe Thr Asn Asp Val Gln Asp Thr Arg Phe
        115                 120                 125 aaa att aat aaa tgg att gaa aat gag aca cat gga aag atc aag aag        432
Lys Ile Asn Lys Trp Ile Glu Asn Glu Thr His Gly Lys Ile Lys Lys
    130                 135                 140 gtg ttg ggc gac agc agc ctc agc tcg tcg gct gtc atg gtg ctg gtg        480
Val Leu Gly Asp Ser Ser Leu Ser Ser Ser Ala Val Met Val Leu Val
145                 150                 155                 160 aac gct gtt tac ttc aaa ggc aaa tgg aaa tcg gcc ttc acc aag act        528
Asn Ala Val Tyr Phe Lys Gly Lys Trp Lys Ser Ala Phe Thr Lys Thr
                165                 170                 175 gat acc ctc agt tgc cgt ttt agg tct ccc acg tgt cct gga aaa gta        576
Asp Thr Leu Ser Cys Arg Phe Arg Ser Pro Thr Cys Pro Gly Lys Val
            180                 185                 190 gtt aat atg atg cat caa gaa cgg cgg ttc aat ttg tct acc att cag        624
Val Asn Met Met His Gln Glu Arg Arg Phe Asn Leu Ser Thr Ile Gln
        195                 200                 205 cag cca cca atg cag gtt ctt gag ctc caa tat cat ggt ggc ata agc        672
Gln Pro Pro Met Gln Val Leu Glu Leu Gln Tyr His Gly Gly Ile Ser
    210                 215                 220 atg tac att atg ctg cct gag gat ggc cta tgt gaa att gaa agc aag        720
Met Tyr Ile Met Leu Pro Glu Asp Gly Leu Cys Glu Ile Glu Ser Lys
225                 230                 235                 240 ctg agt ttc cag aat ctg atg gac tgg acc aat agg agg aaa atg aaa        768
Leu Ser Phe Gln Asn Leu Met Asp Trp Thr Asn Arg Arg Lys Met Lys
                245                 250                 255
```

-continued

```
tct cag tat gtg aac gtg ttt ctc ccc cag ttc aag ata gag aag aat    816
Ser Gln Tyr Val Asn Val Phe Leu Pro Gln Phe Lys Ile Glu Lys Asn
        260                 265                 270 tat gaa atg acg cac cac ttg aaa tcc tta ggc ttg aaa gat atc ttt    864
Tyr Glu Met Thr His His Leu Lys Ser Leu Gly Leu Lys Asp Ile Phe
    275                 280                 285 gat gag tcc agt gca gat ctc tct gga att gcc tct gga ggt cgt ctc    912
Asp Glu Ser Ser Ala Asp Leu Ser Gly Ile Ala Ser Gly Gly Arg Leu
290                 295                 300 tac gta tca aag cta atg cac aag tca ttc ata gag gtc tca gag gag    960
Tyr Val Ser Lys Leu Met His Lys Ser Phe Ile Glu Val Ser Glu Glu
305                 310                 315                 320 ggc act gaa gcc act gct gcc aca gaa aat aac att gtt gaa aag cag   1008
Gly Thr Glu Ala Thr Ala Ala Thr Glu Asn Asn Ile Val Glu Lys Gln
                325                 330                 335 ctt cct gag tcc aca gtg ttc aga gcc gac cgc ccc ttt ctg ttt gtc   1056
Leu Pro Glu Ser Thr Val Phe Arg Ala Asp Arg Pro Phe Leu Phe Val
            340                 345                 350 atc aag aag aat gac atc atc tta ttt act ggc aaa gtc tct tgt cct   1104
Ile Lys Lys Asn Asp Ile Ile Leu Phe Thr Gly Lys Val Ser Cys Pro
        355                 360                 365 tgaaattcga tttggtttcc tatacagtaa caggcatcaa gaa                   1147
```

<210> SEQ ID NO 21
<211> LENGTH: 368
<212> TYPE: PRT
<213> ORGANISM: Mus musculus

<400> SEQUENCE: 21

```
Phe Asp Leu Phe Arg Glu Met Asp Ser Ser Gln Gly Asn Gly Asn Val
1               5                  10                  15

Phe Phe Ser Ser Leu Ser Ile Phe Thr Ala Leu Thr Leu Ile Arg Leu
                20                  25                  30

Gly Ala Arg Gly Asp Cys Ala Arg Gln Ile Asp Lys Ala Leu His Phe
            35                  40                  45

Asn Ile Pro Ser Arg Gln Gly Asn Ser Ser Asn Gln Pro Gly Leu
        50                  55                  60

Gln Tyr Gln Leu Lys Arg Val Leu Ala Asp Ile Asn Ser Ser His Lys
65                  70                  75                  80

Asp Tyr Glu Leu Ser Ile Ala Thr Gly Val Phe Ala Glu Lys Val Tyr
                85                  90                  95

Asp Phe His Lys Asn Tyr Ile Glu Cys Ala Glu Asn Leu Tyr Asn Ala
            100                 105                 110

Lys Val Glu Arg Val Asp Phe Thr Asn Asp Val Gln Asp Thr Arg Phe
        115                 120                 125

Lys Ile Asn Lys Trp Ile Glu Asn Glu Thr His Gly Lys Ile Lys Lys
    130                 135                 140

Val Leu Gly Asp Ser Ser Leu Ser Ser Ala Val Met Val Leu Val
145                 150                 155                 160

Asn Ala Val Tyr Phe Lys Gly Lys Trp Lys Ser Ala Phe Thr Lys Thr
                165                 170                 175

Asp Thr Leu Ser Cys Arg Phe Arg Ser Pro Thr Cys Pro Gly Lys Val
            180                 185                 190

Val Asn Met Met His Gln Glu Arg Arg Phe Asn Leu Ser Thr Ile Gln
        195                 200                 205

Gln Pro Pro Met Gln Val Leu Glu Leu Gln Tyr His Gly Gly Ile Ser
```

-continued

```
             210                 215                 220
Met Tyr Ile Met Leu Pro Glu Asp Gly Leu Cys Glu Ile Glu Ser Lys
225                 230                 235                 240

Leu Ser Phe Gln Asn Leu Met Asp Trp Thr Asn Arg Arg Lys Met Lys
                245                 250                 255

Ser Gln Tyr Val Asn Val Phe Leu Pro Gln Phe Lys Ile Glu Lys Asn
                260                 265                 270

Tyr Glu Met Thr His His Leu Lys Ser Leu Gly Leu Lys Asp Ile Phe
                275                 280                 285

Asp Glu Ser Ser Ala Asp Leu Ser Gly Ile Ala Ser Gly Gly Arg Leu
290                 295                 300

Tyr Val Ser Lys Leu Met His Lys Ser Phe Ile Glu Val Ser Glu Glu
305                 310                 315                 320

Gly Thr Glu Ala Thr Ala Ala Thr Glu Asn Asn Ile Val Glu Lys Gln
                325                 330                 335

Leu Pro Glu Ser Thr Val Phe Arg Ala Asp Arg Pro Phe Leu Phe Val
                340                 345                 350

Ile Lys Lys Asn Asp Ile Ile Leu Phe Thr Gly Lys Val Ser Cys Pro
                355                 360                 365
```

METHOD FOR DETECTING MEGSIN PROTEIN AND USE THEREOF

TECHNICAL FIELD

The present invention relates to a method for evaluating renal function, which comprises measuring the megsin protein in biological specimens such as urine, blood, and so on. Furthermore, the present invention relates to reagents for diagnosing renal function comprising anti-megsin protein antibodies.

The present specification incorporates herein by reference, each in its entirety, the sequence information on the Compact Disks (CDs) labeled Copy 1 and Copy 2. The CDs are formatted on IBM-PC, with operating system compatibility with MS-Windows. The files on each of the CDs are as follows:

Copy 1-Seqlist.txt 11 KB created Apr. 5, 2002; and
Copy 2-Seqlist.txt 11 KB created Apr. 5, 2002.

BACKGROUND ART

Kidney transplantation is the only method to treat terminal renal failure where the renal functions of hemofiltration and detoxication fail completely. However, the supply system supporting renal transplantations in Japan is far from well structured. In addition, social cognition on the transplantation method itself is not advanced. Therefore, the present status is that there is no alternative but to rely on dialysis as a renal replacement treatment.

Today, the number of patients who undergo dialysis is estimated to be approximately 170,000. An average annual treatment cost of about ¥6 million is needed per patient, and it is considered to be one of the biggest reasons that constrain the health insurance system. Furthermore, treatment with dialysis restraints the patient for 4 to 6 hours a day, 2 to 3 days a week, which greatly hampers the social activities of the patient.

Renal failure is a condition patients with renal diseases finally reach. The cause and background leading to renal failure is diverse. There are many cases in which diseases that usually originate outside the kidneys such as drug poisoning, infectious diseases, malignant tumors, diabetes, systemic lupus erythematosus (SLE), cause renal disorders and finally lead to renal failure.

Significant subjective symptoms of renal disorders appear only at late stages, namely only after the condition has almost worsened to renal failure. Therefore, they are easily overlooked, and numerous cases exist where at the point when symptoms appear, the kidney has already suffered an unrecoverable damage. Thus, it is important to discover renal disorders at an earlier stage as possible before the expression of subjective symptoms in order to prevent transition to renal failure, and also to eliminate constraints dialysis treatment puts on public medical insurance finances.

Up to now, the examination of urinary proteins and urinary deposits, the so-called urinalysis, was widely carried out to diagnose renal disorders. However, urinary proteins increase temporarily even in normal healthy persons due to extreme exercise, psychological stress, abundant meat diet, before menstruation, and so on. On the other hand, there are urinary proteins that are unrelated to renal diseases, such as orthostatic albuminuria found mainly in adolescents (in around 0.5% of normal healthy persons). Urinary proteins are also detected in uropathies, bladder disorders, female genital tract disorders, and so on. Thus, it is difficult to make a definite diagnosis of renal disorders only by examining urinal proteins.

Urine deposits are observed with a microscope after centrifugation of urine. However, erythrocyte deposits are also observed in the urine deposits of normal healthy persons, and may also derive from disorders other than renal disorders, such as those of organs related to the urinary tract. Therefore, urine deposits are also not sufficient enough to make definite diagnoses of renal disorders.

A method to diagnose diabetic nephropathy at an early stage is known, which comprises the following steps: (1) assaying albumin that leaked into the urine as an indicator of diabetic nephropathy; and (2) comparing the value with the normal value of a normal healthy person. However, the exact state of diabetic nephropathy cannot be understood since the albumin content in the urine changes even in a normal healthy person.

In addition, serum creatinine (Cr) and blood urea nitrogen (BUN) are assayed to examine the retention of urinary components in the blood, but this assay is also easily influenced by diet. Thus, abnormal values in assays of urinary proteins, as well as serum Cr and BUN does not necessarily imply a renal disorder, and they may frequently occur in normal healthy persons or patients with other diseases.

Further, diagnosis of renal disorders by measuring various substances including urinary $\beta_2$-microglobulin, N-acetylglucosamimidase (NAG), IgG, transferrin, interleukin-6, and such are being tried. However, there are many cases where these measurements do not correspond to the severity of the renal disorder, and therefore, are far from being effective.

Moreover, although a disorder of the whole kidney or involvement of immune reactions may be guessed by measuring these blood components in the urine, it is difficult to identify the site within renal tissue that is affected by the disorder. No examination method other than those mentioned above is known for diagnosing renal disorders and determining the severity with a sufficient sensitivity and specificity. Histological diagnosis by renal biopsy is regarded essential for ultimately diagnosing and determining the severity of renal disorders.

However, renal biopsy is an invasive examination, and frequently accompanies dangers of complications such as hemorrhage, infections, and so on. Further, to conduct the examination, hospitalization in a well-equipped facility having specialists is required, and the physical and social burden on the patient cannot be ignored.

As mentioned above, the examination by urinalysis is simple and convenient, and is also an excellent examination method that enables treatment of a large amount of specimens. However, from the perspective of providing a definite diagnosis of renal disorders, it is far from being satisfactory. On the other hand, renal biopsy is an authentic method to diagnose and determine the severity of renal disorders. However, its use is highly restricted, which cannot be helped. On this account, a method to diagnose renal disorder, which has the simplicity and convenience of a urinalysis, as well as the accuracy of a renal biopsy, has been desired.

Proteins specifically expressed in specific tissues, not only those in the kidney, are often used as indicators of functional disorders of the organ. For example, enzymatic proteins such as LDH and $\gamma$GTP are widely used as markers of hepatic function. However, no protein specific to the kidneys is known which serves as an indicator of their functions.

The present inventors isolated a gene called megsin as a gene especially strongly expressed in mesangial cells by a macroscale DNA sequence analysis and database analysis, and succeeded in obtaining the megsin protein comprising 380 amino acids encoded by the megsin full-length cDNA clone. The present inventors, further found that the human megsin protein belongs to the SERPIN (serine protease inhibitor) superfamily (R. Carrell et al., Trends Biochem. Sci., 10:20 (1985); R. Carrell et al., Cold Spring Harbor Symp. Quant. Biol., 52:527 (1987); E. K. O. Kruithof et al., Blood, 86:4007 (1995); J. Potempa et al., J. Biol. Chem., 269:15957 (1994); E. Remold-O'Donnell, FEBS Let., 315: 105 (1993)) according to an amino acid homology search by the FASTA program using the Swiss Prot database (T. Miyata et al. J. Clin. Invest., 120:828–836 (1998)). These findings were filed as a patent application (PCT/JP98/04269).

Human megsin protein expression was weak in human fibroblasts, smooth muscle cells, endothelial cells, and keratinocytes, and was strong especially in mesangial cells. The comparison of megsin protein expression level in renal tissues from IgA nephropathy patients and normal healthy individuals revealed that the expression level of megsin protein in IgA nephropathy patients was significantly higher. Accordingly, it is possible that megsin protein existing in the urine or blood is useful as a marker of mesangial cell proliferative nephropathy, for example, nephropathies such as IgA nephropathy. There is a possibility that megsin protein gene expression is deeply related with the onset and progression of renal diseases. However, the correlation between megsin protein gene expression and progression of renal disease state was unknown.

DISCLOSURE OF THE INVENTION

An objective of the present invention is to solve problems such as those above, and to provide a method that enables diagnosis of renal diseases and determination of their severity, and also to provide reagents and reagent kits used for the method.

Firstly, the present inventors thought that it is necessary to measure specific proteins related to the state of the disease to make a definite diagnosis of renal disorders and determine their severity, and focused their attention on mesangial cells, which exist in the glomerulus. The mesangium is mapped on the lobule center in the glomerular tuft and is a tissue that functions as a core to bind the lobules together. The mesangium is covered by the glomerular basement membrane. It is composed of cells (mesangial cells), which are divided from the capillary lumen by endothelial cells, and a three-layered amorphous material (mesangial matrix), which is in sequence with the lamina rara interna in the glomerular basement membrane.

The mesangial cells play a pivotal role in maintaining the structure and function of the glomerulus. Their proliferation is thought to be a main factor in the onset of glomerular disorders such as glomerular nephritis and glomerulosclerosis. Furthermore, mesangial cells are targets damaged by all types of nephritis. For example, proliferation of mesangial cells and accumulation of extracellular mesangial matrix is thought to be the first step in the development of glomerulosclerosis in patients suffering from various glomerular diseases, such as chronic nephritis and diabetic nephritis, the two main causes of end-stage renal failure (D. Schlondorff, Kidney Int., 49: 1583–1585, (1996); R. B. Sterzel et al., Glomerular mesangial cell. Immunologic Renal Diseases, 595–626 (1997)) Therefore, it is thought that identification of a gene expressed specifically in mesangial cells and elucidation of its function would be helpful in understanding the biological characteristics of mesangial cells and the causes of diseases relating to mesangial cells, and in turn, treating or diagnosing diseases related to mesangial cells.

It has been reported that steroidal agents are effective for IgA nephropathy with an extreme proliferation of mesangial cells (J. V. Donadio et al., J. Am. Soc. Nephrol. 8:1324–1332 (1997)). However, use of steroidal agents often causes serious side effects, and thus, aimless administration of steroidal agents to types of IgA nephropathy for which steroidal agents are ineffective, should be avoided. Therefore, a matching up with the severity of the tissue such as the degree of proliferation of mesangial cells, and so on, is essential for steroid therapy. Accordingly, a renal function assay that can simply and conveniently evaluate the degree of proliferation of mesangial cells was long desired.

The present inventors assumed that megsin protein gene expression increases in relation to the onset and progress of renal diseases, and in association thereto, megsin protein production increases and leads to a leakage of megsin protein into urine or blood, the amount of which may be related to the progression of disease state. To verify the mechanism, the inventors attempted to measure and compare the concentration or amount of megsin protein in various biological specimens, and thus, accomplished the present invention through the result that renal diseases related to megsin protein can be evaluated by measuring the concentration or amount of the megsin protein. Thus, the present invention relates to a method for evaluating renal functions, as well as to reagents or reagent kits for the method, which are as follows:

(1) a method for evaluating renal functions, which comprises measuring the megsin protein in a biological specimen;

(2) the method for evaluating renal functions of (1), which comprises measuring the megsin protein in a biological specimen, and comparing it with the megsin protein amount in a normal specimen;

(3) the method for evaluating renal functions of (1), wherein the biological specimen is urine;

(4) the method for evaluating renal functions of (1), wherein the megsin protein in the biological specimen is measured by an antigen-antibody reaction using an anti-megsin protein antibody;

(5) the method for evaluating renal functions of (4), wherein the anti-megsin protein antibody is a monoclonal antibody;

(6) a reagent for diagnosing renal functions, which comprises the anti-megsin protein antibody;

(7) the reagent for diagnosing renal functions of (6), wherein the anti-megsin protein antibody is a monoclonal antibody;

(8) a granule for detecting megsin protein in a biological specimen, wherein the granule comprises a solid granule to the surface of which an anti-megsin protein antibody is bound;

(9) the granule for detecting megsin protein of (8), wherein the solid granule is magnetic;

(10) the granule for detecting megsin protein of (8), wherein the relative density of the solid granule is not smaller than 1;

(11) the granule for detecting megsin protein of (8), wherein the anti-megsin protein antibody is a monoclonal antibody;

(12) a method for detecting megsin protein in a biological specimen, comprising the following steps of:

i) contacting the granule for detecting megsin protein with the biological specimen, said granule comprising a solid granule to the surface of which an anti-megsin protein antibody is bound;

ii) contacting the second anti-megsin protein antibody bound to a marker molecule with said granule for detecting megsin protein to which the biological specimen was contacted; and, iii) detecting the marker molecule bound to the megsin protein through the second anti-megsin protein antibody;

(13) the method for detection of (12), wherein the first anti-megsin protein antibody and the second anti-megsin protein antibody are both monoclonal antibodies;

(14) the method for detection of (13), wherein the first anti-megsin protein antibody and the second anti-megsin protein antibody are antibodies having different recognition sites;

(15) the method for detection of (12), wherein the biological specimen is urine;

(16) the method for detection of (12), wherein the biological specimen is blood;

(17) a kit for detecting megsin proteins, which comprises the following elements:

a) magnetic solid granules to which anti-megsin protein antibodies can be bound, b) anti-megsin protein antibodies, which are bound to said magnetic solid granules in advance, or can be bound to them indirectly, and c) a magnet;

(18) the kit for detecting megsin proteins of (17), further comprising an anti-megsin protein antibody to which a marker molecule is bound.

As mentioned above, the megsin protein was isolated as a protein encoded by a gene that is highly expressed in human kidney mesangial cells. The megsin protein of the present invention includes not only a protein having the amino acid sequence of SEQ ID NO: 2 (human megsin protein), but also proteins functionally equivalent thereto. For example, megsin protein homologues from species other than human can be mentioned as proteins that are functionally equivalent. Other examples are precursors and fragments of these homologues. Megsin protein-protease complexes can also be used as indicators of renal functions, as long as they can be detected within biological specimens. Megsin protein homologues of species other than humans can be used as indicators for the evaluation of renal functions in the respective species. Thus, they are useful to understand disease states in renal function disorder models.

Megsin protein homologues from species other than human can be obtained, for example, as follows: First, the homologue cDNA is amplified by PCR utilizing a degenerative primer designed based on the nucleotide sequence of the cDNA encoding the human megsin protein of SEQ ID NO: 1 to correspond to the beginning and end of the ORF. In case where the amplified cDNA is not a full-length cDNA, its upstream nucleotide sequence can be determined by methods such as 5'RACE. For example, RT-PCR is conducted using the mRNA, which is extracted from cultured mesangial cells, as the template for rats. Degenerative primers used can be, for example, the oligonucleotides with the following nucleotide sequences. Part of the structure of the rat homologue megsin protein can be revealed by sequence determination of the clone obtained by such a PCR method. Degenerative primer FY: GTGAATGCTGTG-TACTTAAAGGCAANTGN/SEQ ID NO: 3 (corresponding to 172VNAVYFKGK180) Degenerative primer R21: AANAGRAANGGRTCNGC/SEQ ID NO:4 (wherein R is A or G; corresponding to 357ADHPFLF363)

However, to obtain the 5' regions, it is necessary to conduct a degenerate PCR again by preparing gene specific primers from clone fragments of the rat megsin protein, since only a part of the cDNA can be amplified with these primer pairs. The nucleotide sequences of the primers used, which correspond to the N terminal amino acid sequences of the megsin proteins are as follows: Degenerative primer RM-CtermC1: ATGGCNTCNGCNGCNGC-NAAYGC/SEQ ID NO:5 (wherein Y is T or C; corresponding to the sequence encoding the N-terminus of the megsin protein) RM-MR-A2: CGACCTCCAGAGGCAATTCCA-GAGAGATCAGCCCTGG/SEQ ID NO: 6 RM-MR-A1: GTCTTCCAAGCCTACAGATTTCAAGTGGCTCCTC/ SEQ ID NO: 7 (Each of them is a rat megsin protein specific reverse primer)

The 3'region of the cDNA encoding the rat homologue can be derived by inserting the obtained PCR product into the pGEM-T-easy vector (Promega) to determine the nucleotide sequence. Finally, the nucleotide sequence of the full-length cDNA encoding the homologue can be determined by conducting 5'-RACE and 3'-RACE using a primer designed based on the nucleotide sequence obtained as above. Two gene specific antisense primers, namely RM-PRO1: GCTCAGGGCAGTGAAGATGCTCAGG-GAAGA/SEQ ID NO:8 and RM-PRO2: CTGACGTGCA-CAGTCACCTCGAGCACC/SEQ ID NO: 9, can be used for the 5'-RACE for rats. On the other hand, gene specific sense primer RM-MR-S3: GAGGTCTCAGAAGAAG-GCACTGAGGCAACTGCTGCC/SEQ ID NO:10 can be used in the 3'-RACE. Mouse homologues can be isolated by the same method. The sequence of rat and mouse megsin cDNA nucleotide sequence depicted in SEQ ID NO:18 (rat) and SEQ ID NO:20 (mouse) were determined according to the method above.

The method used in the present invention to measure the megsin protein is not restricted. For example, immunological assays, which make use of the immunological reaction between an antibody for the megsin protein and the megsin protein, are excellent in both specificity and sensibility. Such examples are immunoprecipitation, radioimmunoassay, immunofluorescence assay, enzyme immunoassay, chemiluminescence assay, and immunohistochemistry. Furthermore, the megsin protein can be measured by the Western Blot method utilizing an antibody against the megsin protein. These immunoassays can also be combined, such as performing the Western Blot method after the immunoprecipitation. These assay methods are well known in the technical field of the invention.

Immunohistochemistry is a method where the antibody of the present invention is reacted with an isolated human cell or disrupted cell solution thereof, tissue or disrupted tissue solution thereof, blood serum, pleural effusion, ascites, tears, and such, and further reacted with the anti-mouse IgG antibody or binding fragments, which are labeled with fluorescent substances like fluorescein isothiocyanate (FITC) or with enzymes like peroxidase, and then are observed using a microscope. Each marker substance can be also labeled indirectly by binding streptavidin bound marker substances with biotinylated antibodies. Furthermore, since the megsin protein is a protease inhibitor, it can be detected using its inhibition activity on protease as the indicator. Alternatively, the megsin protein can be assayed utilizing its affinity towards the protease.

The source or preparation method of the antibody, which is essential for immunological assays of the megsin protein, can be any so long as the antibody can recognize the detection target, which is the megsin protein. Thus, antibodies to be used include polyclonal antibodies, monoclonal antibodies, mixtures thereof, etc. Furthermore, fragments containing the variable region of the antibody molecule are included. The antibody against megsin protein can be obtained, for example, as follows. For example, antibodies used in the present invention comprise those antibodies raised against the protein having the amino acid sequence of SEQ ID NO:2. The antibody (for example, polyclonal antibody or monoclonal antibody) or the antiserum against the megsin protein or partial amino acids sequence thereof can be prepared according to conventional methods for antibody or antiserum preparation using megsin proteins, oligopeptides comprising a partial amino acid sequence thereof, as well as fusion proteins, such as c-myc-(His)$_6$-Tag-megsin protein and MBP-megsin protein, as the antigens. For example, monoclonal antibodies can be prepared following the methods below. In cases where synthetic peptides with partial amino acid sequence are used as immunogens, it is generally convenient to use highly hydrophilic amino acid sequences that are specific to megsin protein. Such amino acid sequences include those shown in SEQ ID NO:11 to 17, which were used in the examples. Among these sequences, the amino acid sequences shown in SEQ ID NO:12 (human), SEQ ID NO:14 (human), or SEQ ID NO:17 (rat) especially yielded antibodies with good reactivity to the glomerulus tissue.

The megsin protein of the present invention or a synthetic peptide having a partial amino acid sequence of the present megsin protein, is administered alone or together with a carrier or diluent to a warm-blooded animal at a site capable of producing antibodies. Synthetic peptides used as immunogens are in the form peptides bound to carrier proteins such as bovine thyroglobulin and keyhole limpet hemocyanin. To enhance the antibody productivity, the complete Freund's adjuvant or incomplete Freund's adjuvant can be administered together with the antigen. Immunization is performed once every 1 to 6 weeks, a total of about 2 to 10 times, in general. Warm-blooded animals to be used are, for example, monkeys, rabbits, dogs, guinea pigs, mice, rats, sheep, goats, and domestic fowls, preferably mice or rats. Monoclonal antibody-producing cells can be prepared by selecting immunized warm-blooded animals, such as mice, in which an antibody titer is detected, obtaining the spleen or lymph nodes from the animals 2 to 5 days after the final immunization, and fusing the antibody producing cells contained in these tissues with myeloma cells. Reacting the labeled megsin protein described below with the antiserum, and measuring the activity of the label bound to the antibody enables measurement of the antibody titer in the antiserum.

A monoclonal antibody of the present invention that does not crossreact with proteins other than megsin protein can be obtained by selecting an antibody that recognizes epitopes specific to megsin protein. In general, an epitope specific to the protein comprises at least 7 or more continuous amino acid residues, preferably 10 to 20 amino acids in the amino acid sequence of the protein. Therefore, for example, a monoclonal antibody recognizing an epitope comprising peptides having an amino acid sequence selected from the amino acid sequence of SEQ ID NO: 2, SEQ ID NO: 19(rat), or SEQ ID NO: 21(mouse), and comprising at least 7 continuous amino acid residues can be a monoclonal antibody specific to the megsin protein. Conserved amino acid sequences among the amino acid sequences of SEQ ID NO: 2, SEQ ID NO: 19 (rat), and SEQ ID NO: 21 (mouse) can be selected to choose epitopes common to the megsin protein family. If a region contains amino acid sequences specific to all sequences, a monoclonal antibody capable of recognizing different species can be selected.

An anti-MEGSIN protein monoclonal antibody can be separated and purified according to a separation and purification method for immunoglobulin, similar to the separation and purification of polyclonal antibodies. The known purification methods include, for example, salting out, alcohol precipitation, isoelectric point precipitation, electrophoresis, adsorption and desorption method by ion exchangers (for example, DEAE), ultra centrifugation, gel filtration, or specific purification methods whereby an antibody is exclusively collected, for example, methods whereby an antigen is collected using an antigen binding solid phase or active adsorbent, such as Protein A or Protein G, and thereafter the binding is dissociated to obtain the antibody.

Monoclonal antibodies and polyclonal antibodies obtained in such a manner that recognize the megsin protein of the present invention, can be used for the diagnosis and treatment of diseases relating to mesangial cells. Examples of methods that use these antibodies to measure the megsin protein include a sandwich assay, which comprises reacting the megsin protein with an antibody binding to an insoluble carrier and a labeled antibody and detecting MEGSIN protein in the sandwiched complex produced by the reaction, or a competitive method comprising competitively reacting labeled human urine-derived megsin protein and human urine-derived megsin protein in a sample with an antibody to measure human urine-derived megsin protein in the sample based on the labeled antigen amount that reacted with the antibody.

The assaying of human urine-derived megsin protein by the sandwich method is conducted by a 2 step method in which an immobilized antibody is reacted with human urine-derived megsin protein, unreacted materials are completely removed by washing, and a labeled antibody is added to form the immobilized antibody-labeled human urine-derived MEGSIN protein antibody complex, or one step method in which the immobilized antibody, the labeled antibody, and human urine-derived MEGSIN are mixed at the same time.

Examples of insoluble carriers used for the assay include, for example, polystyrene, polyethylene, polypropylene, polyvinyl chloride, polyester, polyacrylate, nylon, polyacetal, synthetic resin such as fluoride resin, etc., polysaccharides such as cellulose, agarose, etc., glass, metals, etc. The form of the insoluble carrier can be varied and includes a shape like a particle, tray, sphere, fiber, stick, board, container, cell, test tube, etc. The antibody-adsorbed carrier should be stored in a cool place in the presence of appropriate preservatives, such as sodium azide.

On the other hand, solid granules are known as reagents used to evaluate the fertility of human sperm cells. These granules comprise on their surfaces monoclonal antibodies that specifically react with human sperm cells having undergone the acrosome reaction (Japanese Patent No.2651249). This granule used for sperm fertility detection is a solid granule to which a monoclonal antibody that specifically reacts with human sperm cells having undergone the acrosome reaction is bound. The fertility of human sperm cells can be evaluated by reacting sperm cells with the granules and counting sperm cells bound to the granules. The fertility can be tested readily and safely without the use of complicated techniques like radioactivity, fluorescence, and so on. Samples of small quantities can be assayed by using magnetic solid granules since the granules can be aggregated easily by using a magnet. The present inventors found out that it is possible to detect megsin protein more easily and accurately by applying this technique.

Antibodies can be immobilized by known chemical binding or physical adsorption methods. Chemical binding methods include, for example, a method using glutaraldehyde, the maleimide method using N-succinimidyl-4-(N-maleimidomethyl)cyclohexane-1-carboxylate, N-succinimidyl-2-maleimidoacetate, etc., and the carbodiimide method using 1-ethyl-3-(3-dimethylaminopropyl)carbodiimide hydrochloride, etc. Further examples are, the maleimidobenzoyl-N-hydroxysuccinimidoester method, the N-succinimidyl-3-(2-pyridyldithio)propionate method, the bisdiazolated benzidine method, and dipalmityllysine method. Alternatively, a complex, which is prepared by reacting two different antibodies having different epitopes with the substance to be detected, can be captured with a third antibody immobilized by the above method.

The label is not limited, so long as it is useful in immunoassays. Specifically, enzymes, fluorescent substances, luminescent substances, radioactive substances, metal chelates, etc. can be used. Preferable labeling enzymes are, for example, peroxidase, alkaline phosphatase, β-D-galactosidase, malate dehydrogenase, *Staphylococcus* nuclease, delta-5-steroid isomerase, α-glycerol phosphate dehydrogenase, triosephosphate isomerase, horseradish peroxidase, asparaginase, glucose oxidase, ribonuclease, urease, catalase, glucose-6-phosphate dehydrogenase, glucoamylase, and acetylcholine esterase, etc. Preferable fluorescent substances include, for example, fluorescein isothiocyanate, phycobiliprotein, rhodamine, phycoerythrin, phycocyanin, allophycocyanin, and orthophthalaldehyde. Preferable luminescent substances include, for example, isoluminol, lucigenin, luminol, aromatic acridiniumester, imidazole, acridinium salt and its modified ester, luciferin, luciferase, and aequorine. Preferable radioactive substances include, for example, $^{125}$I, $^{127}$I, $^{131}$I, $^{14}$C, $^{3}$H, $^{32}$P, $^{35}$S, etc.

Methods for binding the above labels are known. Specifically, direct and indirect labeling can be used. The commonly used direct labeling method is the method in which an antibody or an antibody fragment is chemically covalent-bound to a label using a cross-linking agent. Crosslinking agents include N,N'-orthophenylenedimaleimide, 4-(N-maleimidomethyl) cyclohexanoate N-succinimide ester, 6-maleimidohexanoate N-succinimide ester, 4,4'-dithiopyridine, and other known crosslinking agents. The crosslinking agent can be reacted with enzymes and antibodies by known methods depending on the characteristics of the cross-linking agent. An example of the indirect labeling method comprises binding an antibody to a low molecular weight hapten such as biotin, dinitrophenyl, pyridoxal, or fluorescamine, and indirectly labeling the antibody with the binding partner to the hapten. Avidin and streptavidin can be used as a recognition ligand for biotin, whereas dinitrophenyl, pyridoxal, or fluorescamine are labeled with antibodies recognizing these haptens.

Horseradish peroxidase can be used as an enzyme for labeling antibodies. This enzyme is useful because it can react with many substrates and be easily bound to antibodies by the periodate method. Occasionally, antibody fragments, for example, Fab', Fab, F(ab')$_2$ are used as antibodies. Both polyclonal and monoclonal antibodies can be labeled with an enzyme by the same method. Enzyme-labeled antibodies obtained using the above crosslinking agent can be purified by known methods such as affinity chromatography, etc. to serve as more sensitive immunoassay systems. Purified enzyme-labeled antibodies are stored with a preservative such as thimerosal and a stabilizer such as glycerol. Labeled antibodies can be lyophilized and stored in the cool and dark place for a long time.

When the label is an enzyme, its substrate and, if necessary, a coloring agent is used for measuring its activity. When peroxidase is used as an enzyme, $H_2O_2$ is used as the substrate solution, and 2,2'-azino-di-[3-ethylbenzothiazolinesulfonic acid] ammonium salt (ABTS), 5-aminosalicylic acid, orthophenylenediamine, 4-aminoantipyrine, or 3,3', 5,5'-tetramethylbenzidine, etc. are used as coloring agents. When alkaline phosphatase is used as the enzyme, orthonitrophenylphosphate, paranitrophenylphosphate, etc. can be used as substrates. When β-D-galactosidase is used as the enzyme, fluorescein-di-(β-D-galactopyranoside), 4-methylumbelliferyl-β-D-galactopyranoside, etc. can be used as substrates. The present invention also includes an immunoassay reagent for megsin comprising labeled or immobilized monoclonal or polyclonal antibodies. The present invention further includes a kit comprising this reagent and an indicator for detection labels and a control sample, etc.

Any biological sample such as body fluid including blood plasma, serum, blood, urine, tissue fluid, or cerebrospinal fluid, etc. can be used as samples for measuring the megsin protein of the present invention, as long as they contain megsin protein or its precursor or a fragment. Among these biological samples, megsin protein can be detected with high frequency especially in urine, accompanied by a proliferation and activation of mesangial cells. Therefore, measurement of megsin in urine is useful as a marker for mesangial proliferative nephropathy, such as IgA nephropathy.

Evaluation of renal functions as used herein means to comprehend the condition of mesangial cells, which is an important cell constructing kidney tissue, and to determine the presence or severity of a renal disease causing abnormalities in mesangial cells. Renal disease as used herein refers to any disease causing an abnormality in mesangial cells. More specifically, IgA nephropathy, acute glomerulonephritis, focal sclerosing glomerulopathy, membranoproliferativeglomerulonephritis, diabeticnephritis, lupus nephritis, and soon, can be mentioned as such diseases. The condition of renal functions affected by these renal diseases can be evaluated by the method of the present invention. Among the above diseases, the present method for evaluating renal function is especially useful as a marker for mesangial cell proliferative nephropathy, such as the IgA nephropathy. Moreover, the method of the present invention for evaluating renal function may be applied not only to determine the existence or severity of a renal disease, but also to evaluate a therapeutic effect or make a prognosis. In addition, the method of the present invention for evaluating renal function enables the exclusion of diseases not ascribable to the proliferation of mesangial cells like acute pyelonephritis, chronic pyelonephritis, minimal-change nephritic syndrome, chronic glomerulonephritis, renal amyloidosis, etc.

To evaluate renal functions according to the present invention, a biological specimen from an individual whose renal function should be tested is obtained and the concentration of megsin protein therein is measured following the above-mentioned methods. Preferably, the amount of megsin protein is determined from the measured concentration and the volume, and compared to that of a normal healthy person. To calculate the amount of megsin protein using urine as the sample, all urine of a day is pooled and the amount of urine is measured. Thereby, it is possible to determine the amount of megsin protein in a day's urine. Alternatively, it is possible to presume the amount by creatinine correction, even when the urine is sampled occasionally. The term "creatinine correction" refers to a method to correct the influence of dilution (or concentration) of the object component due to the changes in urine amount based on the creatinine concentration. The creatinine amount excreted daily into the urine is constant. Based on this fact, the percentage occasionally collected urine occupies in the daily total excretion is calculated from the creatinine concentration, and the concentration of the object component in the same urine is converted into the total excretion of a day. Alternatively, correction methods generally used in the diagnosis of renal functions such as weight correction is applied to presume the amount in blood. Weight correction is a method, wherein the amount of blood component is calculated based on the volume presumed from the weight of the individual from whom the blood was taken.

Alternatively, changes in renal function can be also followed in a time course without having to convert into amounts by observing the changes of megsin protein concentration in a biological specimen derived from a certain individual. Alternatively, an abnormality in renal function can be determined by configuring the normal values for megsin protein concentration in body fluids of specific species or groups like the race, and then, comparing the megsin protein concentration (or amount) of an individual with the normal value.

The biological specimen used in the present invention can be urine or blood. Urine is more preferable since it can be collected in a noninvasive manner and is at the same time a sample that reflects the condition of renal functions directly. Although blood must be collected with some invasiveness, since megsin protein is a protein specific to the kidney, an abnormality of the measured value closely relates to an abnormality of renal function. Thus, a high specificity can be expected if the amount of megsin protein in blood and urine is used as indicators of renal function. Compared to the currently widely used method of screening for renal function disorder using urinary proteins as indicators, a more specific screening method with a superior sensibility can be expected by utilizing the megsin protein as the indicator. A method for evaluating renal functions by measuring the megsin protein in urine based on the immunological method for measuring the megsin protein using a monoclonal antibody will be explained in detail below.

(A) Preparation of the Antibody (1) Immunization of the Animal and Preparation of Antibody-Producing Cells The immunization of the animal is conducted, for example, as follows. A mammal, such as a rat, mouse, and so on, is immunized with the human megsin protein purified according to conventional methods (for example, T. Miyata et al., J. Clin. Invest., 120:828–836 (1998)). It is preferable to immunize animals of the same strain as the animal strain from which the permanently proliferating cell used during cell fusion is obtained. For example, mice at the age of 8 to 10 weeks are preferable. Mice of both genders will do. The immunization is conducted as follows: (1) the purified human megsin protein is mixed to an emulsion with an appropriate adjuvant (for example, Freund's complete adjuvant, aluminum hydroxide gel-pertussis vaccine, etc.), and (2) administered to the animal subcutaneously, intraperitoneally, intravenously, etc. Repeating this immunization process 2 to 5 times, with an interval of 1 to 2 weeks. The final immunization is accomplished by an intraperitoneal administration of 0.5 to 2 µg human megsin protein to the animal. Polyclonal antibodies are obtained from the body fluid of the thus immunized animal. 3 to 7 days after each immunization process, blood is collected from venus plexus of the eyeground, and the antibody titer of the serum is measured by the protein A rosette assay (Eur. J. Immunol., 4:500–507 (1974)) described below. The antibody or the antibody-producing cell is harvested as the antibody titer had elevated enough.

The protein A rosette assay is, for example, performed as follows: (1) 72 well Terasaki Plate (Falcon) is coated with the human erythroblast cell line K562 (Japanese Cancer Research Resources Bank (JCRS)); (2) samples diluted with PBS (sodium dihydrogen phosphate 2.90 g, potassium monohydrogen phosphate 0.20 g, sodium chloride 8 g, potassium chloride 0.2 g, distilled water 1 L) are added; (3) the plate is left standing for 30 minutes at 37° C. in a $CO_2$ incubator; (4) the wells are washed with PBS; (5) sheep erythrocytes coated with protein A (Amersham Pharmacia Biotech) are added; and, (6) the formed rosettes are observed with a microscope.

Antibody-producing cells are harvested from the above human megsin protein immunized animal. Antibody-producing cells can be obtained from the spleen, lymph nodes, peripheral blood, and so on. However, the spleen is especially preferred. For example, 3 to 4 days after the final immunization, the spleen is excised aseptically, cut in a Minimal Essential Medium (MEM) (Nissui Pharmaceutical), detach tissues and cells with a tweezer, and after centrifugation at 1,200 rpm for 5 minutes the supernatant is discarded. Then the pellet is treated with Tris-HCl buffer (pH 7.65) for 1 to 2 minutes, and erythrocytes are eliminated. After washing 3 times with MEM, spleen cells used for cell fusion are obtained.

(2) Preparation of Permanently Proliferating Cells

Any cell with permanent proliferation ability can be used as the permanently proliferating cell for the fusion. However, myeloma cells are generally used. It is preferable to use cells derived from the same specie as that from which the antibody-producing cell was obtained. For example, in the case of mouse, the following cell lines are known as 8-azaguanine resistant mouse (BALB/c)-derived myeloma cell lines.

P3-X63Ag8-U1 (P3-U1) (Current. Topics in Microbiol. Immunol., 81:1–7, (1978)),

P3/NS1/1-Ag4-1 (NS-1) (Eur. J. Immunol., 6:511–519, (1976)),

SP2/0-Ag14 (SP-2) (Nature, 276:269–270, (1978)),

P3-X63-Ag8653 (653) (J. Immunol., 123:1548–1550, (1979), and

P3-X63-Ag8 (X63) (Nature, 256:495–497, (1975))

These permanently proliferating cell lines are subcultured in 8-azaguanine media (normal media, RPMI-1640 medium supplemented with glutamine (1.5 mM), 2-mercaptoethanol ($5\times10^{-5}$ M), gentamicin (10 µg/mL) and fetal calf serum (FCS, CLS) (10%), supplemented with 8-azaguanine (15 µg/mL)), and passaged to normal media 3 to 4 days before cell fusion to ensure a cell count of $2\times10^7$ cells at the day of cell fusion.

(3) Cell Fusion

Fusion of cells is, for example, performed as follows. The antibody-producing cell obtained in (1), and the permanently proliferating cell prepared in (2) are mixed at a cell rate of 5 to 10:1 after washing well with MEM or PBS. After centrifugation at 1,200 rpm for 5 minutes, the supernatant is removed and the precipitated cells are detached well. 0.1 to 1.0 mL/$10^8$ cells are added to a mixture of 1 to 4 g polyethylene glycol-1000 (PEG-1000), 1 to 4 mL MEM, and 0.5 to 1.0 mL dimethyl sulfoxide, and the mixture is kept at 37° C. while stirring to fuse the cells. Then, the mixture is diluted by adding 3 mL MEM few times every 10 minutes to a total volume of 50 mL MEM to quench the cell fusion reaction. Next, the supernatant is discarded after centrifugation (1,500×5 min), cells are gently tapped, 100 mL normal medium (RPMI-1640 media, 10% FCS) is added, and the cells are suspended by gentle pipetting with a measuring pipette. 100 µL suspension is dispensed to each well of a 96 well culture plate, and incubated at 37° C. for 3 to 5 days in an 5% $CO_2$ incubator. 100 µL of HAT medium (normal medium supplemented with =hypoxanthine ($10^{-4}$ M), thymidine (1.5×$10^{-5}$ M), and aminopterin (4×$10^{-7}$ M)) is added to each well of the culture plate, and incubated further for 3 days. Thereafter, half of the culture supernatant is discarded and the same amount of HAT medium is added thereto every three days. The incubation is continued for about 2 weeks at 37° C. in a 5% $CO_2$ incubator.

(4) Screening and Cloning of the Hybridoma

Supernatants are removed from wells in which fusion cells are observed to grow in colonies, same amount of HT medium (HAT medium without aminopterin) is added, and the cells are incubated for 4 days. Part of the culture supernatant is harvested to measure the antibody titer against megsin protein by the aforementioned protein A rosette assay. The antibody titer can be also assayed by other methods like the following. For example, 1) by adding the hybridoma culture supernatant to a solid phase (e.g. microplate), where the megsin protein antigen is attached directly or together with a carrier; 2) adding anti-immunoglobulin antibody (if the cell for cell fusion is derived from mouse, anti-mouse immunoglobulin antibody is used) labeled with radioactive substances or enzymes, or protein A; and 3) detecting the anti-megsin protein monoclonal antibody bound to the solid phase. The antibody titer can be also assayed by: 1) adding the hybridoma culture supernatant to a solid phase, where an anti-immunoglobulin antibody or protein A is attached; 2) adding megsin protein labeled with radioactive substances or enzymes, and 3) detecting the anti-megsin protein monoclonal antibody bound to the solid phase.

Cloning is repeated 4 times by limiting dilution method for wells in which the production of antibodies that react to the megsin protein was observed, and cell lines, which show stable megsin protein antibody titers are selected as anti-megsin protein monoclonal antibody producing hybridoma cell lines.

(5) Preparation of the Monoclonal Antibody

The monoclonal antibody is produced by incubating the thus obtained hybridomas in vitro or in vivo. In case where the incubation is conducted in vivo, the hybridoma is transplanted to appropriate animals. It is preferable to use the same kind of animal as that from which the spleen cells for cell fusion were taken. For example, 2 to 4×$10^6$ cells of anti-megsin protein monoclonal antibody producing hybridoma cells obtained in (4) is administered intraperitoneally to each 8 to 10 week old BALB/c female mouse treated with pristane (reared for 2 weeks after intraperitoneal administration of 0.5 mL 2,6,10,14-tetramethylpentadecane-pristane). Subsequently, after 2 to 3 weeks, the abdomen of the mouse enlarges due to the accumulation of ascites, which contain the monoclonal antibody at a high concentration, in the visceral cavity of the mouse. The ascites are then collected from the mouse, centrifuged (3,000 rpm×5 min) to remove solid matters, and the IgGs are purified. Alternatively, the hybridoma is cultured in vitro in a serum-free and an appropriate amount of antibody secretes to the supernatant. The ascites or the culture supernatant is salted out with 50% ammonium sulfate, and then dialyzed for 1 to 2 weeks with PBS. The dialyzed fraction is passed through a protein A Sepharose column, and the IgG fraction is collected to obtain a purified monoclonal antibody.

The isotype of the antibody is determined according to the Ouchterlony method (double immunodiffusion) ("Menekigaku jikken nyumon, Seibutsugaku jikkenhou 15" (A laboratory manual for immunology, Biochemical experimentation 15), Gakkai Shuppan Center, p74 (1981)). The quantity of the protein is calculated by the Folin method and by the absorbance at 280 nm (1.4 ($OD_{280}$)≈immunoglobulin 1 mg/mL).

(6) Characterization of the Monoclonal Antibody

The characterization of the monoclonal antibody obtained above can be performed by, for example, (1) immunoprecipitation method utilizing human lymphocyte derived cell lines, such as HSB-2, K562, and soon, the cell surface of which is labeled with iodine (J. Immunol., 138: 2850–3855 (1987)); (2) enzyme immunoassay (ELIZA) (J. Immunol., 142: 2743–2750 (1989)); and such.

(7) Preparation of Labeled Monoclonal Antibody

The obtained purified monoclonal antibody may be enzyme labeled by methods like glutaraldehyde method (Immunochem., 6: 43 (1969)), periodic acid method (J. Histochem. Cytochem., 22: 1084 (1974)), maleimide method (J. Biochem., 79: 233 (1976)), pyridil disulfide method (Biochem. J., 173: 723 (1978)), etc.

For example, the periodic acid method is performed as follows: (1) periodic acid (38.5 mg/mL) is added to the peroxidase solution (4 mg/mL) while stirring; (2) reacted at room temperature for 20 minutes; (3) the buffer is exchanged using PD-10 (Amersham Pharmacia Biotech) substituted with 1 mM acetate buffer (pH 4.5); (4) 40 µL of 0.2 M sodium hydroxide is added; (5) 10 mg of monoclonal antibody dialyzed with 10 mM carbonate buffer is added (pH 9.5); (6) react at room temperature for 2 hours; (7) after the reaction is completed, the mixture is cooled on ice; (8) 100 µL solution of sodium boron hydride (4 mg/mL) is added and reacted for 2 hours; (9) the reaction solution is changed to PBS using PD-10; (10) centrifuged at 3,000 rpm for 30 minutes; (11) the supernatant is gel filtrated using Sephacryl S200HR26X30 (Amersham Pharmacia Biotech); (12) the labeled monoclonal antibody fraction is obtained by detecting the absorbance at 403 and 280 nm; (13) bovine serum albumin (10 mg/mL) is added to the obtained fraction; (14) stored at −20° C., and diluted with PBS-Tween (Trademark) 20 before usage.

(B) Preparation of Granules for Detection

The granules for detection used herein may be prepared by physically or chemically binding anti-megsin protein monoclonal antibody to appropriate granules, for example, gel for chromatography. The method used in the present invention for binding the antibody to chemically activated granules is a preferable method due to the expected binding stability. More specifically, the method for binding the antibody used in the present invention to granules that are actively tosylated by p-toluenesulfonyl chloride can be given.

Granules to be used are made of glass, agarose, Sepharose, agarose filled porous diatomite, hydrophilic copolymerized acrylic gel, polystyrene, and so on. Use of magnetic granules enables collection of the granules with the use of magnet, and so on, thereby allowing detection of small quantity samples. For example, by placing substances capable of being magnetic (e.g. $Fe_2O_3$) in the core of the granules, it is possible to make the granules superparamagnetic. Such granules are commercially available as solid phases for immunological analyses. The granule may take any appropriate form such as a sphere, amorphous fracture, etc., however, sphere shaped granules are preferred. There is no limitation on the particle size of the granule, and an average particle size, for example, of 5 to 1000 µm can be given. Furthermore, the use of granules with larger specific gravity than that (about 1) of the reaction solution facilitates collection of the granules, giving an effect similar to that when magnetic granules are used. Furthermore, the use of granules with larger specific gravity is more advantageous for antibodies whose binding is easily disassociated, because gentle centrifugation conditions are possible when collecting the granules.

Anti-megsin protein antibodies can be bound to the granules not only by direct binding but also by indirect binding. For example, if a mouse monoclonal antibody is used as the antibody, an antibody that recognizes mouse IgG is attached to the granule and the mouse antibody can be bound to the granule indirectly. Such antibodies are called secondary antibodies. Indirect binding can be also accomplished by utilizing protein A or protein G, which bind to the constant region of immunoglobulin, or by capturing avidin-attached granules with biotinylated antibodies, and so on. To chemically bind the secondary antibody, protein A, or protein G to the granule, it is preferable to activate the granules before binding. As an activation method of the granule, any appropriate activation method used to conjugate proteins to the granule can be selected. Such activation methods include, the tosyl chloride method, bromcyane method, bromacetyl method, glutaraldehyde method, etc. There are also commercially available activated granules. Activation and binding of these activated granules to proteins, such as secondary antibodies, protein A, protein G, and such, can be performed according to conventional methods.

In addition, granules conjugated to secondary antibodies, protein A, protein G, and so on are also commercially available. Granules mentioned below are known as commercially available granules.

Dynabeads™ M-450, M-280 provided by Veritas, and imported by Dynal Japan
  Sheep anti-mouse IgG coated type
  Goat anti-mouse IgG coated type
  Sheep anti-rat IgG coated type
  Sheep anti-rabbit IgG coated type
Polyscience Inc.
  Goat anti-mouse IgG (H&L) carboxylate beads
  Goat anti-rabbit IgG (H&L) carboxylate beads
  Protein A carboxylate beads
  Goat anti-rabbit IgG (H&L) micromagnet particle
  Goat anti-rabbit IgG (H&L) micromagnet particle
  Protein A micromagnet particle
  Sheep anti-mouse IgG (H&L) micromagnet particle The binding of the present antibody to the granules above is conducted as follows: (1) unspecific binding is prevented by treating the granules suspended in appropriate media with a protein solution, and (2) mixing the ascites containing the antibody or the purified antibody solution.

(C) Detection Method

The detection method of the present invention is accomplished by collecting blood or urine from the subject, and using the supernatant after centrifugation as the specimen. The centrifugation of urine is done to separate the precipitate, and the supernatant of urine left standing still, or urine from which the precipitate is removed by filtration can be also used. Specimen diluted with the detection granule prepared above and the labeled antibody obtained in (7) are mixed, and then, incubated at room temperature for 2 hours. After the reaction has come to an end, the mixture is washed, and the substrate solution is added for chromogenic reaction. Then, the mixture is centrifuged to remove the granules, the supernatant is transferred onto a microplate, and the absorbance is measured. A specimen from a normal healthy person is also assayed according to the same method, and the absorbance is compared. Mere comparison of the concentration of the megsin protein, as well as a comparison of the absolute quantity of megsin protein in the body fluid, which is obtained by multiplying with the volume of body fluid of the individual, or comparisons based on of other similar corrected values might be performed.

(D) Kit

The materials used to perform the experiment above can be supplied as a kit. The kit may comprise a detection granule, to which the antibody is conjugated as described above, and a magnet. It may also include an antibody labeled with a marker molecule. Further, the kit of the present invention may include test tubes, centrifugation tubes, other similar containers, pipettes or other suction instruments, and microscopes. Furthermore, enzyme substrates necessary for detecting the label, and positive or negative standard samples may be combined. Solid granules and antibodies, which are the raw material for the detection granules mentioned above, may be included instead of the detection granules. The invention is described in detail with reference to the examples below, but it is not to be construed as being limited thereto.

BEST MODE FOR CARRYING OUT THE INVENTION

EXAMPLE 1

Mesangial Cells

Figure 1:
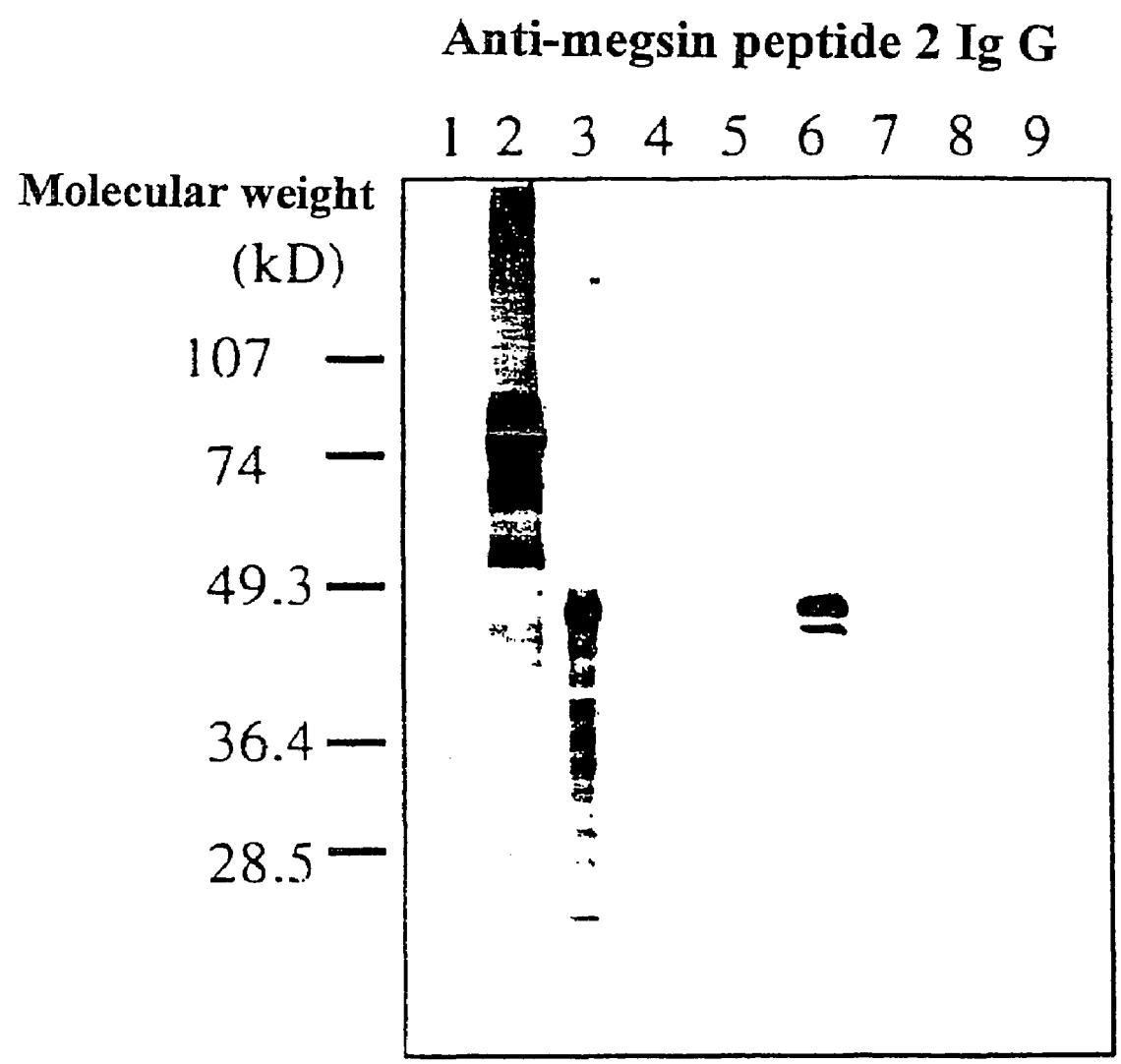
FIG. 1 shows the result of Western blotting using a polyclonal antibody specific to synthetic peptide-2, which has a partial amino acid sequence of megsin protein (SEQ ID NO: 12), as the antigen. Each lane represents the following:
  1: MBP
  2: MBP-megsin protein
  3: His-megsin protein
  4: MBP-PAI II
  5: megsin protein expressed in CHO cells
  6: body fluid of the silkworm infected with a recombinant virus transfected with the megsin protein gene
  7: body fluid of the silkworm infected with a recombinant virus without transfection by megsin protein gene
  8: body fluid of the virus-uninfected silkworm
  9: normal human serum

Human mesangial cells and CHO (Chinese hamster ovary) cells obtained from TaKaRa (Tokyo, Japan) were cultured in Dulbecco's modified Eagle's medium containing 10% fetal calf serum at 37° C. in a 5% $CO_2$ incubator. Human mesangial cells were subcultured for 7 to 10 generations, and then used for the following experiments.

EXAMPLE 2

Production of Polyclonal Antibodies Against Synthetic Peptides of the Megsin Protein Polyclonal antibodies against megsin protein were produced by using regions having low identity with other members of the serpin family and which are hydrophilic as the immunogens. More specifically, polypeptides with the following amino acid sequences derived from the amino acid sequence of human megsin (SEQ ID NO: 2) and rat megsin (SEQ ID NO: 19) were selected:

| Position from N-terminus | Amino acid sequence | SEQ ID NO/No. |
| --- | --- | --- |
| 16–30 | FREMDDNQGNGNVFF | 11/1 |
| 72–86 | SQSGLQSQLKRVFSD | 12/2 |
| 339–354 | ATGSNIVEKQLPQSTL | 13/3 |
| 257–272 | NLMEWTNPRRMTSKYV | 14/4 |
| 342–356 | SNIVEKQLPQSTLFR | 15/342 |
| 74–87 | LGLQYQLKRVLAD | 16/rat1 |
| 341–354 | ESNIVEKLLPESTV | 17/rat2 |

Peptides having the amino acid sequences shown above with a C attached to the N-terminus (for peptide 3 at its C-terminus) were synthesized on the automatic synthesizer model 432A (Perkin Elmer, Foster City, Calif.). After purifying the synthetic peptide by reverse phase HPLC, the peptide was freeze-dried and used in a competitive experiment to confirm immunity and immunological specificity.

Each of these synthetic peptides were bound to bovine thyroglobulin (Sigma) using N-(6-maleimidocaproyloxy) succinimide (Dojindo Molecular Technologies Inc.), were dialyzed against 0.85% NaCl solution, and were mixed well with the adjuvant (Difco) to emulsion, and were administered subcutaneously to a rabbit. 3 weeks after priming (20 μg/rabbit), second immunization (50 μg/rabbit) was carried out, and thereafter, four immunizations (50, 100, 200 μg/rabbit) were performed every two weeks. Freund's complete adjuvant was used for the priming, and thereafter, incomplete Freund's adjuvant was used. After 41 days and 55 days, the antibody titer of the serum was evaluated by enzyme-linked immunosorbent assay (ELISA) to confirm that the serum obtained by blood sampling reacts with synthetic peptide. To conduct primary reaction, 100 μL of continuously diluted antiserum was added to each well of the 96 well plate, in which 50 ng/well antigen had been immobilized. After washing, the HRP conjugated goat anti-rabbit IgG (Cappel) was reacted against it in the second reaction. After washing, the coloring reaction was done using ortho-phenylenediamine (Wako Pure Chemical Industries, Ltd.) as the substrate and absorbance was measured at 492 nm. An increase in antibody titer was confirmed.

EXAMPLE 3

Purification of Polyclonal Antibodies Against Synthetic Peptides of Megsin Protein The polyclonal antibodies against each synthetic peptide of megsin protein were purified by immunoaffinity chromatography according to conventional methods (Cell Engineering supplement "Jikken Protocol Series Kou-peptide Jikken protocol (Experimental protocol series: Anti-peptide experimental protocol)", Shujun-sha, Japan). More specifically, the method was carried out as follows: 1) an affinity column was prepared by immobilizing each synthetic peptide to FMP (2-fluoro-1-methylpyridinium toluene-4-sulfonate) activated Cellulofine (Seikagaku Corp.); 2) after the rabbit serum showing increased antibody titer was diluted with PBS (−), the antibody was purified by affinity using the peptide column. It was demonstrated that the obtained purified antibody is specific to the megsin protein, by confirming its reaction against megsin protein fusion protein by Western blotting (FIGS. 1 to 4).

EXAMPLE 4

Preparation of Antibodies Against Rat Megsin Synthetic Peptides

Each rat megsin synthetic peptide was bound to keyhole limpet hemocyanin (KLH) (Calbiochem-Novabiochem, La-Jolla, Calif.). Namely, KLH suspended in 0.05 M sodium phosphate buffer (pH 7.2) was reacted with m-maleimidobenzoyl-N-hydroxysuccinimidoester (MBS) diluted in dimethylformamide by stirring 30 minutes at room temperature. The reactant was dialyzed with 0.05 M sodium phosphate buffer (pH 6.0) and was used as the KLH-MB. Then, the obtained KLH-MB was incubated with the above-mentioned peptide suspended in distilled water. Half of 0.2 M disodium hydrogenphosphate was added to KLH-MB and was stirred for 3 hours at room temperature. Following the reaction, it was dialyzed with sodium phosphate buffer and was finally freeze-dried. The rabbit was immunized with the obtained KLH conjugated synthetic peptide and the adjuvant. Freund's complete adjuvant (FCA) (DIFCO Laboratories, USA) was used for the priming, and Freund's incomplete adjuvant (DIFCO Laboratories, USA) was used for the immunization that followed. Immunization was conducted 5 times with 2 to 3 weeks intervals. IgG was purified from antiserum using Protein A affinity column (Pharmacia Biotech, Uppsala, Sweden). Serum was also obtained from rabbits before immunization, and the IgG was purified in the same manner.

EXAMPLE 5

Studies on Reactivity of the Rabbit Polyclonal Anti-Megsin Peptide IgG

The reactivity of the rabbit IgG, which was produced using megsin protein as the immunogen, was studied using the following various proteins as antigens. MBP-megsin protein and His-megsin protein were prepared as follows: 1) the coding region was amplified by PCR based on the nucleotide sequence of megsin gene described in SEQ ID NO: 1; 2) the amplified products were inserted into maltose binding protein fusion protein expression vector pMAL-c (New England Biolab) to obtain vectors that express the fusion protein of MBP and megsin protein; 3) *E. coli* were transformed with this vector; and then, 4) the MBP-megsin protein was obtained by purifying the expression product from the disrupted cell solution by affinity chromatography utilizing amylose, and such. To obtain His-megsin protein, a fusion protein expression vector containing aforementioned megsin gene in the vector ptrcHisA (Invitrogen), which expresses the inserted gene as a fusion protein with a histidine tag, was constructed. This vector was transformed into *E. coli* JM109, and following the induction of expression by IPTG, the His-megsin protein was obtained as a fusion protein purified by nickel column and such from the disrupted cell solution.

Then, recombinant megsin was expressed in CHO cells as follows. The c-myc tag and histidine tag was ligated to the N-terminus of the full-length coding region of megsin cDNA by the induction of mutation utilizing PCR. The tag conjugated megsin cDNA was cloned into mammalian cell expression vector pREP9 (Invitrogen). PREP9 containing human megsin cDNA was transformed into CHO cells ($10^5$ cells), which were cultured on a 6 well plate at 37° C. in a 5% $CO_2$ incubator, using LipofectAMINE (GIBCO BRL, Gaithersburg, Md.). Stable transformants were selected with 0.5 mg/ml geneticin disulfate (Wako Pure Chemical Industries). Then, the c-myc-histidine tag conjugated megsin recombinant (CHO megsin) was purified from the culture supernatant by $(His)_6$ affinity column.

The megsin protein(+)virus-infected silkworm body fluids refers to body fluids of a silkworm, which is infected with megsin gene introduced virus according to known methods (J. General Virology 78: 3073–3080 (1979)). On the other hand, megsin protein(−)virus-infected silkworm body fluids refers to body fluids of a silkworm, which is infected with a virus without the megsin gene. The gene encoding megsin necessary for designing these megsin recombinants can be synthesized by PCR using mRNA of the mesangial cell as the template, or obtained from the megsin gene cloning vector (Accession No. FERM BP-6518) constructed by the inventors.

Reactivity against plasminogen activator inhibitor-1 (PAI I), MBP-plasminogen activator inhibitor-2 fusion protein (MBP-PAI II), and so on was also observed. These proteins were selected to confirm the cross-reactivity of the antibody, and share some extent of homology with the megsin protein.

MBP-megsin protein,

His-megsin protein,

MBP-PAI II,

PAI I, megsin protein expressed in CHO cells, megsin protein (+) virus-infected silkworm body fluid, megsin protein (−)virus-infected silkworm body fluid, non-virus-infected silkworm body fluid, and human serum albumin.

Each protein solution was treated with same amount of sample buffer (0.25% Tris-HCl, 2% SDS, 30% glycerin, 10% β-mercaptoethanol, 0.025% Bromophenol Blue) (Daiichi Pure Chemicals), heated at 100° C. for 5 minutes, and the proteins were separated by SDS-polyacrylamide gel electrophoresis (SDS-PAGE) (Laemmli, U. K., Nature 227: 680–685 (1970)). The proteins separated by SDS-PAGE was blotted on poly vinylidene difluoride (PVDF) membrane (BioRad) with a constant voltage of 100 V for 1 hour, using the blotting solution (25 mM Tris-HCl, 192 mM glycine, 20% methanol, pH 8.3). Following the washing of the blotted PVDF membrane with distilled water, the membrane was blocked for 3 hours in TTBS solution containing 5% Block Ace. After washing the PVDF membrane with TTBS (20 mM Tris, 500 mM NaCl, 0.05% Tween20, pH 7.5), it was reacted at 4° C., overnight with the primary antibody, rabbit polyclonal anti-megsin peptide IgG, diluted in TTBS. Then it was detected with Amplified Alkaline Phosphatase Immunoblot Kit (BioRad). That is, it was first incubated for 1 hour with TTBS diluted biotinylated goat anti-rabbit IgG at room temperature, then reacted with streptavidin-biotinylated alkaline phosphatase complex, which was prepared in advance by incubating streptavidin and biotinylated alkaline phosphatase for 1 hour at room temperature. The PVDF membrane was washed in TTBS, and then incubated with the substrate (nitro blue tetrazolium and 5-bromo-4-chloro-3-indolyl phosphate, p-toluidine salt solution) for about 30 minutes at room temperature tovisualizetheantibodyboundtotheprimaryantibody. The reaction was quenched by reacting with a sufficient amount of distilled water.

The results are shown in FIGS. 1 to 4. The antibodies reacted in each figure were obtained using the following substances as the immunogen.

FIG. 1. immunogen: megsin peptide-2

Figure 2:
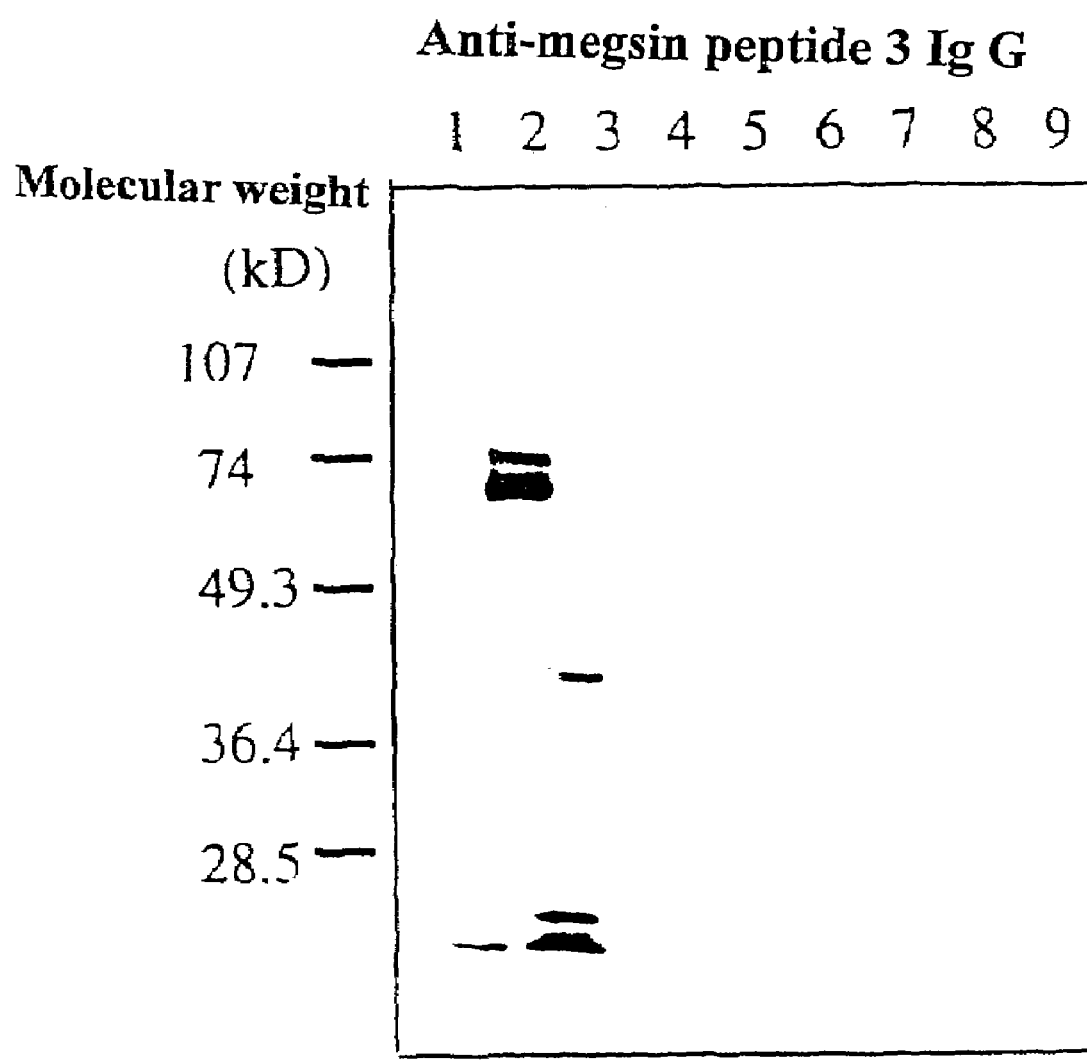
FIG. 2 shows the result of Western blotting using a polyclonal antibody specific to synthetic peptide-3, which has a partial amino acid sequence of megsin protein (SEQ ID NO: 13), as the antigen. Each lane represents the same proteins as in FIG. 1.

FIG. 2. immunogen: megsin peptide-3

Figure 3:
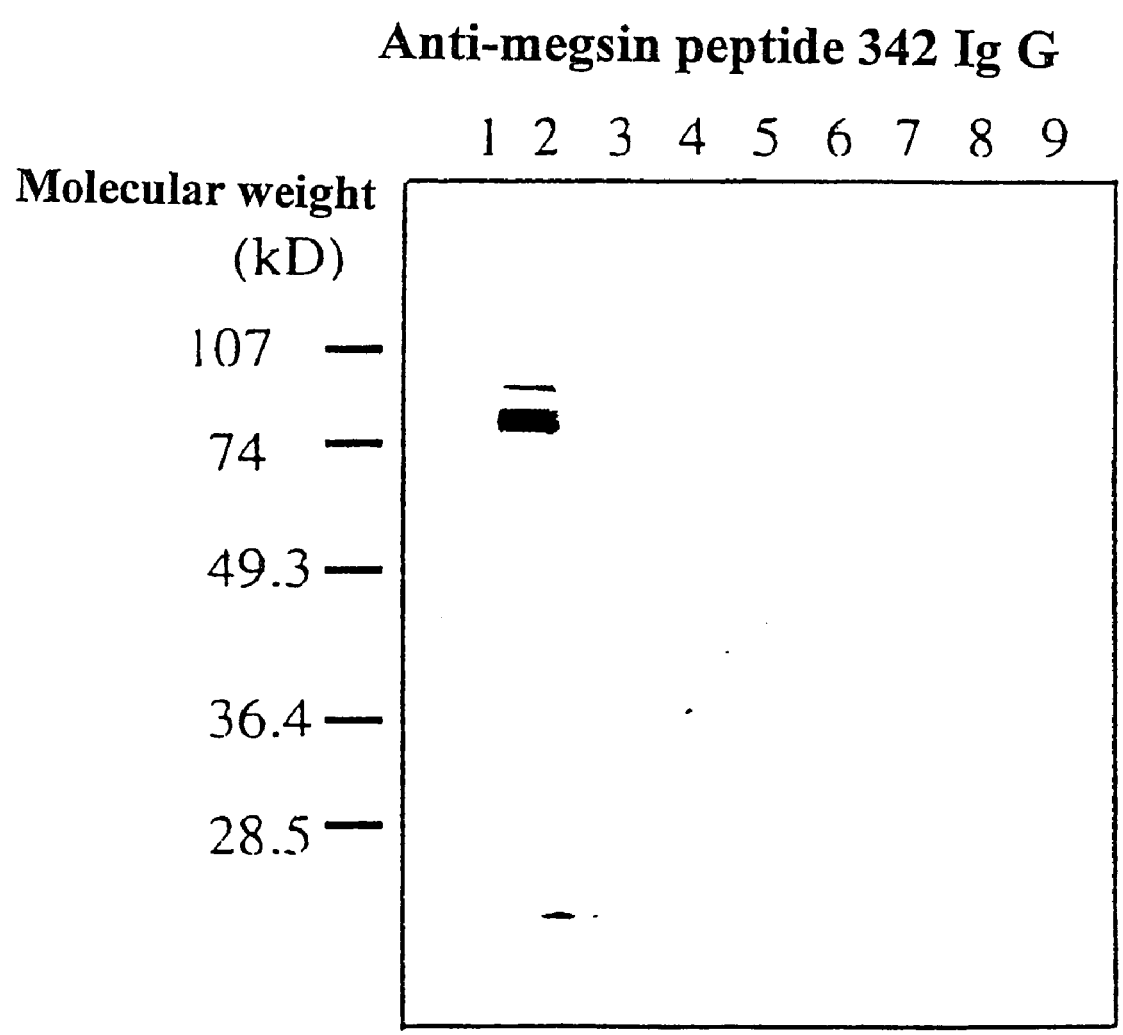
FIG. 3 shows the result of Western blotting using a polyclonal antibody specific to synthetic peptide-342, which has a partial amino acid sequence of megsin protein (SEQ ID NO: 15), as the antigen. Each lane represents the same proteins as in FIG. 1.

FIG. 3. immunogen: megsin peptide-342, and

Figure 4:
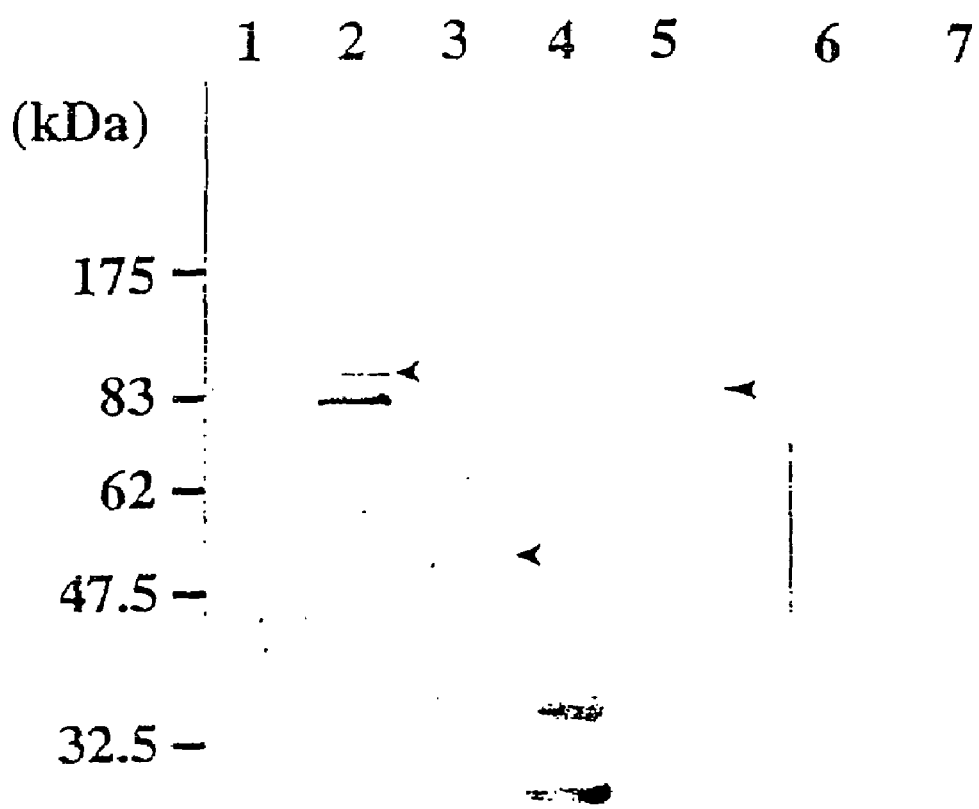
FIG. 4 shows the result of Western blotting using a polyclonal antibody specific to MBP-megsin protein, as the antigen. Each lane represents the same proteins as in FIG. 1.

FIG. 4. immunogen: MBP-megsin protein

EXAMPLE 6

Enzyme Labeling of Affinity Purified Anti-Megsin Peptide IgG

The affinity purified anti-megsin peptide IgG obtained in Example 3 was labeled with alkaline phosphatase using a commercial labeling kit (AP labeling kit: Boehringer-Mannheim) following the instructions in the kit. Biotinylation was performed with another labeling kit (ECL protein biotinylation module: Amersham Pharmacia Biotech) following the instructions.

EXAMPLE 7

Measurement of urinary megsin protein by ELISA

Figure 5:
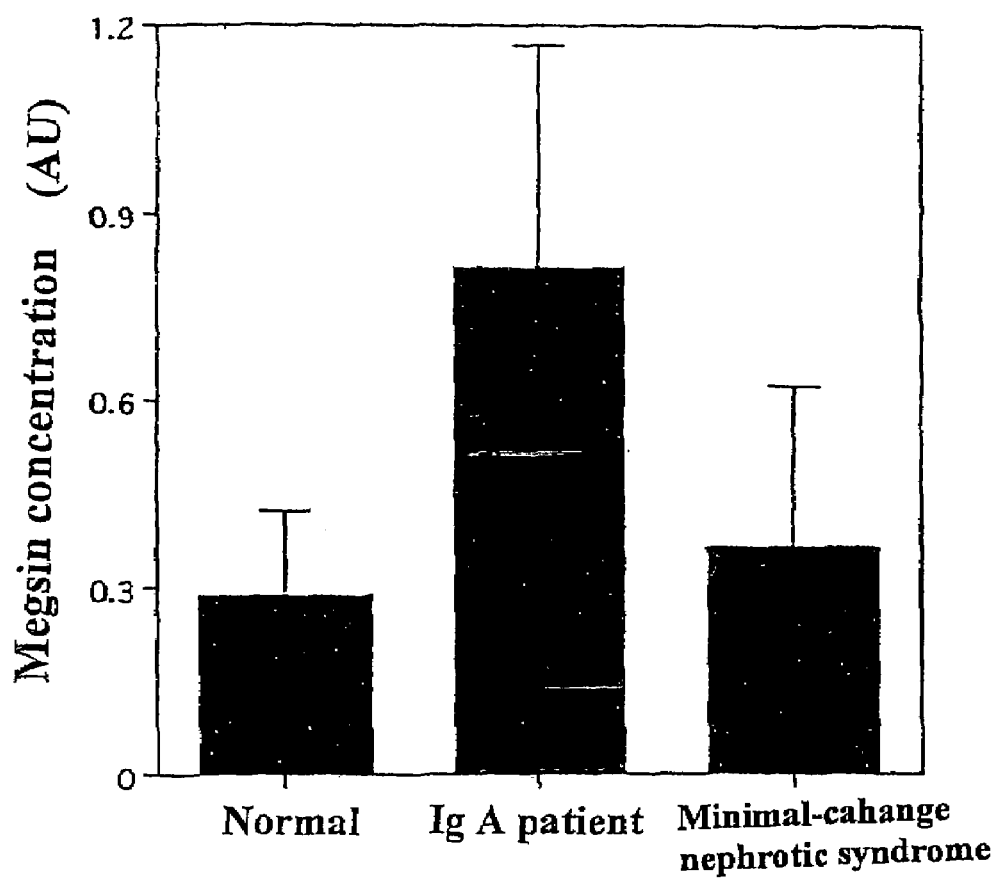
FIG. 5 is a graph showing assay results of urinary megsin proteins by ELISA. The vertical axis shows assayed value of megsin protein (creatinine ratio:AU). Urine from normal healthy person (16 samples), from patients with IgA nephropathy (24 samples), and from patients with minimal-change nephritic syndrome (24 samples) was used as specimens.

Urine from 16 normal healthy persons, 24 IgA nephropathy patients, and 24 minimal-change nephritic syndrome patients were centrifuged to exclude the insoluble material. This was then concentrated using an ultrafilter, with a molecular weight cut-off of 5,000 (Ultarafree, Millipore). Each well of the 96 well ELISA plate was coated with rabbit polyclonal anti-megsin peptide-2 IgG. 120 µL PBS (−) was poured into each well, then 120 µL concentrated urine was added thereto and was left standing overnight at 4° C. The wells were washed with PBS (−), and Block Ace (Dainippon Pharmaceutical) was added to conduct blocking for 2 hours at room temperature. The wells were then washed with PBS (−) containing 0.05% (w/v) Tween20 (Wako Pure Chemical), alkaline phosphatase labeled rabbit polyclonal anti-megsin peptide-1 antibodies were added, and left standing for an hour at room temperature. After washing with Tween-PBS, 100 µL of coloring substrate solution (1 mg/mL orthophenylenediamine (Wako Pure Chemical)—1 M diethanolamine (Wako Pure Chemical) buffer (pH 9.8)) was added to each well. After reacting at room temperature, the reaction was quenched with 50 µL/well 1 N sodium hydroxide, and the absorbance at 405 nm was measured with a microplate reader (Spectra MAX 250, Molecular Devices). The megsin protein concentration in the urine was determined from the calibration curve. The creatinine concentration in the same urine specimen was determined with the commercially available creatinine-measuring reagent (measuring reagent for automated analyzer "Dia"-Crea, Dia Pharmaceutical), and the amount of megsin protein was corrected as creatinine ratio. The result is shown in FIG. 5. A significant difference in megsin concentration was observed between that of the normal healthy persons and patients of IgA nephropathy ($p<0.001$), or between that of IgA nephropathy patients and minimal-change nephritic syndrome patients ($p<0.001$).

Since a significant difference between normal healthy persons and IgA nephropathy patients was observed, onset of renal disorders could be confirmed by measuring urinal megsin protein. Furthermore, due to the significant difference observed between patients of IgA nephropathy and minimal-change nephritic syndrome, it was revealed that these diseases could be distinguished by measuring urinal megsin protein according to the present invention. These diseases cannot be distinguished by conventional screening methods using urinary protein as indicators, because positive results would be shown for both diseases.

Furthermore, in comparisons of urinary megsin protein concentration without creatinine correction, although megsin protein concentration tends to be higher for patients with renal disorders, it seemed difficult to prove a statistically significant difference with a small number of examples. Thus, it is preferable to compare the amounts by methods like creatinine correction and such, when implementing the measurement of megsin protein in urine according to the present invention.

EXAMPLE 8

Detection and Assay of Urinary Megsin Protein by Western Blotting

Urine from 8 normal healthy persons and 9 IgA nephropathy patients were centrifuged, after discarding insoluble material, the solution was concentrated with an ultrafilter with a molecular weight cut-off of 5,000 (Ultrafree, Millipore). The concentrated urine was treated with same amount of sample buffer (0.25% Tris-HCl, 2% SDS, 30% glycerin, 10% β-mercaptoethanol, 0.025% Bromophenol Blue) (Daiichi Pure Chemicals), heated at 100° C. for 5 minutes, and separated in a gradient gel with a gel gradient of 4 to 20% (Daiichi Pure Chemicals) by SDS-polyacrylamide gel electrophoresis (SDS-PAGE) (Laemmli, U. K. (1970) Nature 227, 680–685). The protein separated by SDS-PAGE was blotted on poly vinylidene difluoride (PVDF) membrane (BioRad) with constant voltage of 100 V for 1 hour, using the blotting solution (25 mM Tris-HCl, 192 mM glycine, 20% methanol, pH 8.3). Following the washing of the blotted PVDF membrane with distilled water, the membrane was blocked for 3 hours in TTBS solution containing 5% Block Ace. After washing the PVDF membrane with TTBS (20 mM Tris, 500 mM NaCl, 0.05% Tween20, pH 7.5), it was reacted overnight at 4° C. with a primary antibody solution, rabbit polyclonal anti-megsin peptide IgG diluted in TTBS.

Figure 6:
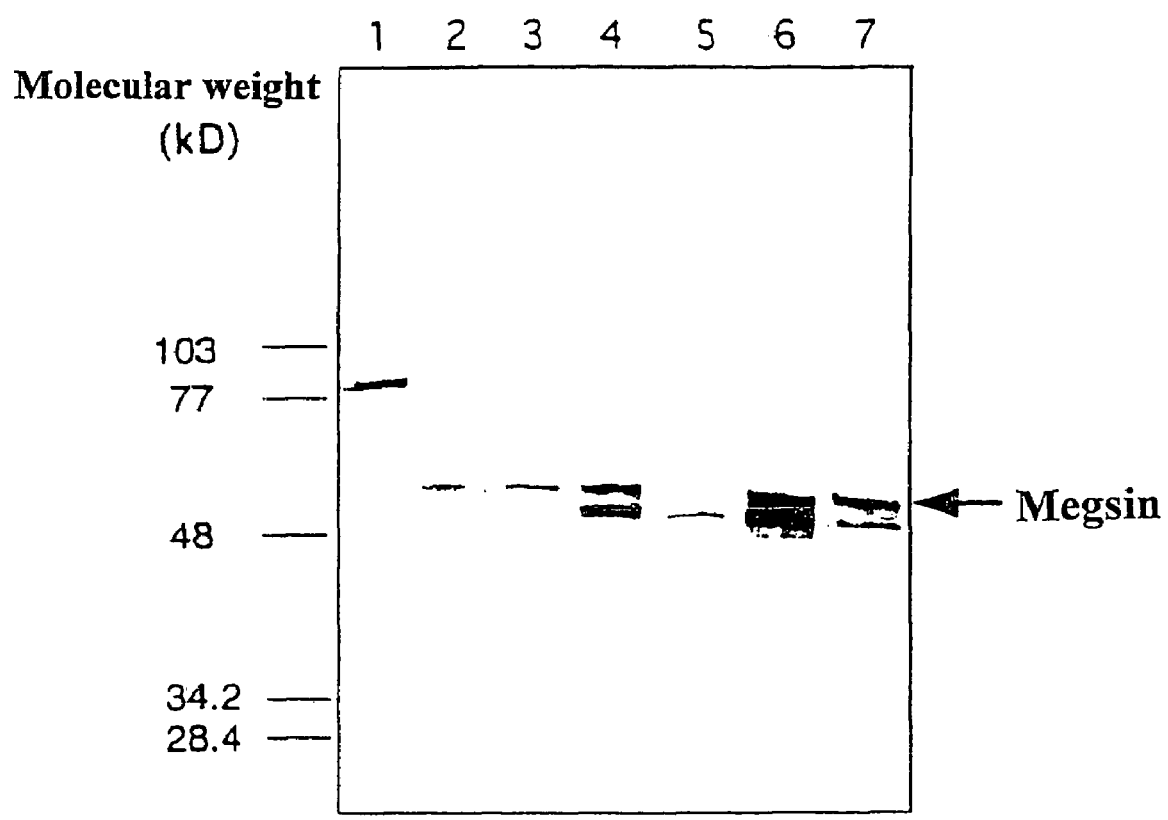
FIG. 6 shows the assay result of Western blotting on urinary megsin protein. Each lane represents the following:
1: MBP-megsin protein
2 to 5: concentrated urine from normal healthy persons
6 and 7: concentrated urine from patients with IgA nephropathy

Then it was detected with Amplified Alkaline Phosphatase Immuneblot Kit (BioRad). That is, it was first incubated for 1 hour with biotinylated goat anti-rabbit IgG diluted with TTBS at room temperature, then reacted with streptavidin-biotinylated alkaline phosphatase complex, which was prepared in advance by incubating streptavidin and biotinylated alkaline phosphatase for 1 hour at room temperature. The PVDF membrane was washed in TTBS, and then incubated with the substrate (nitro blue tetrazolium and 5-bromo-4-chloro-3-indolyl phosphate, p-toluidine salt solution) for about 30 minutes at room temperature to visualize the antibody bound to the primary antibody. The reaction was quenched by reacting with a sufficient amount of distilled water. The visualized bands were quantitatively analyzed using Densitograph gel documentation system (AE-6920M-05, Atto) and densitograph analyzing software (AE-6920WSE/MSE, Atto). The result (electrophoretogram) is shown in FIG. 6. The measurements of the image analyzer are as follows. Dense bands were observed for IgA nephropathy patients compared to the bands of concentrated urine of normal healthy persons. It was revealed that quantitative measurement of the megsin protein is possible by quantitatively analyzing the density of these bands. Measurement result of the image analyzer

| Lane | Measurement result |
|---|---|
| 1 | Molecular weight marker |
| 2 | 8.5 |
| 3 | 5.2 |
| 4 | 13.8 |
| 5 | 4.8 |
| 6 | 32.8 |
| 7 | 15.1 |

EXAMPLE 9

Preparation of Granules for Detection

The granules for detection of the present invention were produced by conjugating anti-megsin peptide IgG to commercially available magnetic granules through anti-mouse IgG antibody. DynabeadS™ M-450 tosylactivated (homogenous tosyl activated paramagnetic polystyrene granules: Dynal Biotech) was used as the granules of the present invention, and a 1 mM hydrochloric acid solution thereof was washed once with sterile distilled water and then with 0.2 M boric acid buffer (pH9.5). Then, anti-megsin peptide IgG antibody was dissolved in 0.2 M boric acid buffer (pH 9.5) at a concentration of 150 µg/mL, and this solution was added to an equal amount of the activated granule suspension (antibody/granule=75 µg/15 mg). Then, the mixture was incubated for 24 hours at 22° C. with gentle stirring. The antibody-conjugated granules were collected with a magnet, and the supernatant was discarded leaving the granules attached to the magnet. Then the granules were washed as follows:

(1) with 5 mL 0.1 M PBS (pH7.0) for 10 minutes, (2) with 5 mL 1 M ethanolamine-HCl (pH 9.5) for 2 hours, (3) with 5 mL 0.05 M Tris (pH 7.5) containing 0.1 M sodium chloride, 0.1% bovine serum albumin (BSA), and 0.1% Tween20 for 12 hours, and (4) with 5 mL buffer of (3) without Tween20 for 2 hours.

Thereafter, granules were collected with a magnet, supernatant was discarded, and the granules were suspended in PBS (−)/BSA containing 10% Block Ace at a concentration of about $4 \times 10^8$ granules/mL (30 mg/mL) Thus obtained IgG-conjugated granules are stable for at least 6 months at 4° C.

EXAMPLE 10

Measurement of Urinary Megsin Protein by the Magnetic Granule Method

Megsin protein concentration of occasional urine samples from 12 normal healthy persons and 24 patients with different renal diseases were measured by the magnetic granule method utilizing antibody-conjugated granules prepared in Example 9. 12 of the renal disease patients were affected with IgA nephropathy, and the other 12 were affected with minimal-change nephritic syndrome. The urinary samples were kept at −80° C., and were thawed before measurement. They were centrifuged at 3,000 rpm for 5 minutes, and the supernatant thereof were used as the sample. The measurement was carried out as follows:

500,000 magnetic granules conjugated to the primary antibody (rabbit polyclonal anti-megsin peptide-2 antibody) were put into a tube (1.5 mL) blocked beforehand with Block Ace (Dainippon Pharmaceutical). 500 µL of each urinary sample and equal amounts of alkaline phosphatase labeled rabbit polyclonal anti-megsin peptide-1 antibodies dialyzed with PBS (−) were mixed, and reacted for 2 hours at room temperature while rotating. Then, after centrifugation at 3,000 rpm for 5 minutes, leaving the granules attached to the magnet, the supernatant was discarded, and 1 mL washing solution (0.05% (w/v) Tween 20 (Wako Pure Chemical) containing PBS (−) (pH7.4) (Tween-PBS)) was added and the granules were washed while stirring. The washing was repeated 4 times, and then, 100 µL substrate solution was added to react for 20 to 30 minutes with stirring. 1 M diethanolamine (Wako Pure Chemical) buffer (pH 9.8) containing 1 mg/mL orthophenylenediamine (Wako Pure Chemical) was used as the substrate solution. Following the completion of the reaction, the reaction was quenched with 50 µL 1 N sodium hydroxide, and absorbance at 405 nm was measured. The urinary megsin protein concentration was calculated from the calibration curve. Creatinine concentration of the same urinary sample was measured as in Example 7, and the megsin protein concentration was corrected as creatinine ratio.

According to the result of the measurement, urinary megsin protein measurement values (creatinine correction value: AU) of IgA nephropathy patients were distributed in the top region compared to those of the normal healthy person. Additionally, the urinary megsin protein measurement values of IgA nephropathy patients were also higher than those of minimal-change nephritic syndrome patients. Thus, according to the present invention, it is possible not only to decide whether a person is affected by a renal disorder, but definitely identify the state of the renal disorder.

EXAMPLE 11

Immunohistochemical Staining of Renal Tissue Using Megsin Peptide Antibody

Renal tissues were taken from 3 IgA nephropathy patients (2 male, 1 female: age 21 to 48 years old) with their permission. Tumor-less tissues taken from surgically excised renal tissues from patients with renal tumors, were used as normal renal tissue specimens. No abnormality was observed in urine of the patient who provided the normal renal tissue, and from a histological point of view, those who showed an abnormality in glomus were excluded. Tissues from organs other than kidneys, were also obtained as controls from patients with their permission. Rat kidney and other organs were obtained from normal Wister rats (male, 8 weeks old).

The renal tissue was embedded in frozen tissue embedding agent (O.C.T. compound) according to the conventional method. 4 µm frozen sections were prepared from the frozen embedded tissues using cryostat Thus prepared frozen sections were mounted on a slide coated with 3-aminopropylethoxysilane (Sigma) (immobilization with 4% paraformaldehyde, 15 minutes).

The frozen sections were washed with PBS containing 0.5% Tween 20, blocked with 4% skim milk, and incubated overnight with anti-megsin peptide-2 antibody and anti-megsin peptide-4 antibody in a humidification chamber at 4°

C. Tissue sections were washed and incubated at room temperature for 2 hours with peroxidase labeled goat anti-rabbit IgG antibody (DAKO) diluted to 1:100. 3,3'-diaminobenzidine solution containing 0.003% oxygenated water was used for the detection of peroxidase. The nuclei were stained with hematoxylin. Hematoxylin/eosin staining was performed following conventional methods.

Figure 7:
FIG. 7 shows a microscopic photograph of immunostained kidney tissue of patients with IgA nephropathy.

The micrograph (ECLIPSE E400: magnification of 80 diameters, Nikon) of the immunohistochemically stained renal tissue of the IgA nephropathy patient is shown in FIG. 7. As is apparent from the picture, the human renal glomeruli tissue has a site that is stained with the peptide antibody of the present invention. Particularly, a notable positive staining was observed inside the mesangial cell and mesangial matrix, but the urinary tubule was not stained.

Figure 8:
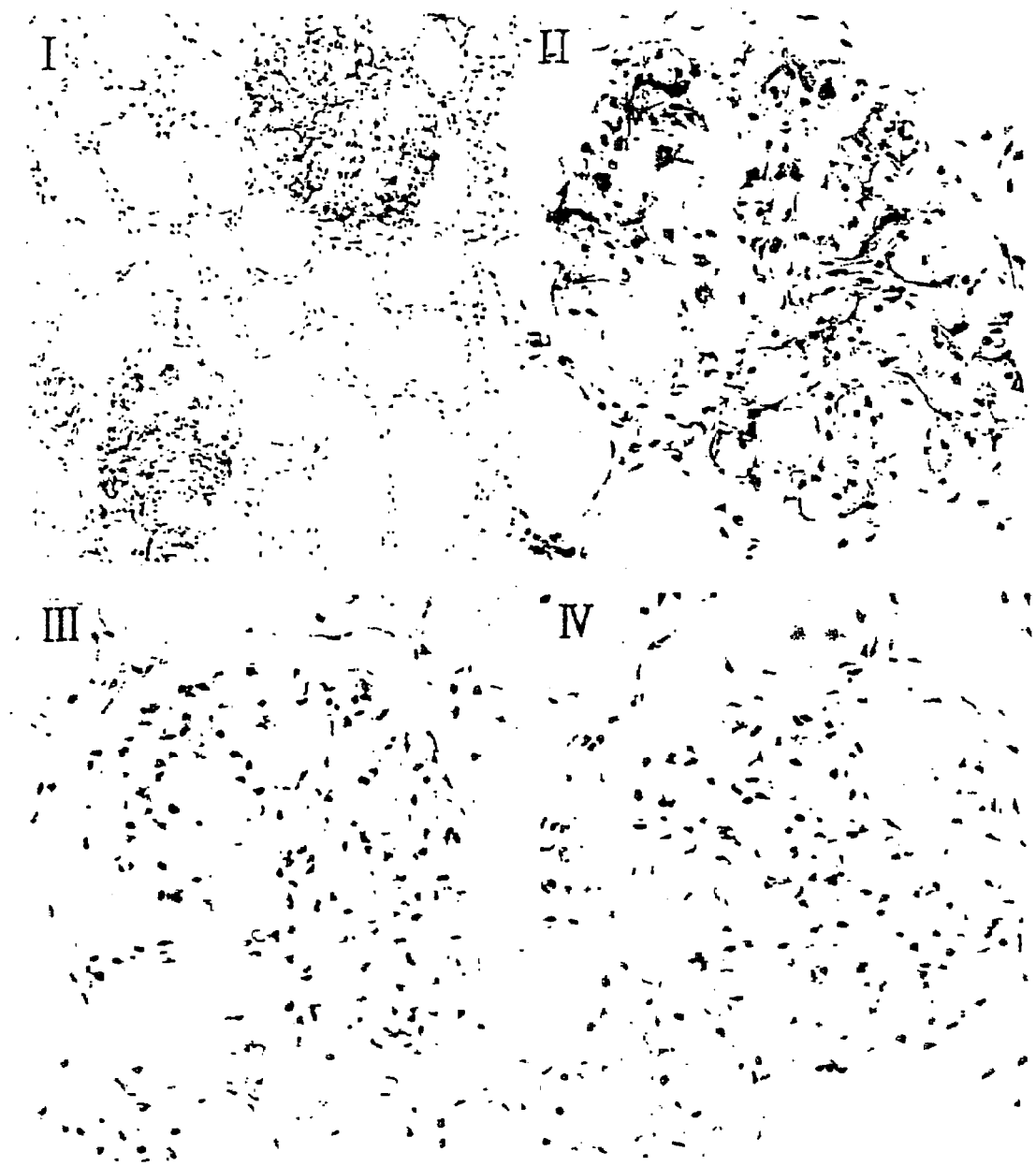
FIG. 8 shows a microscopic photograph of immunostained human kidney tissue of a normal person. I is a magnification of 33 times, and II to IV is of 80 times.
Figure 9:
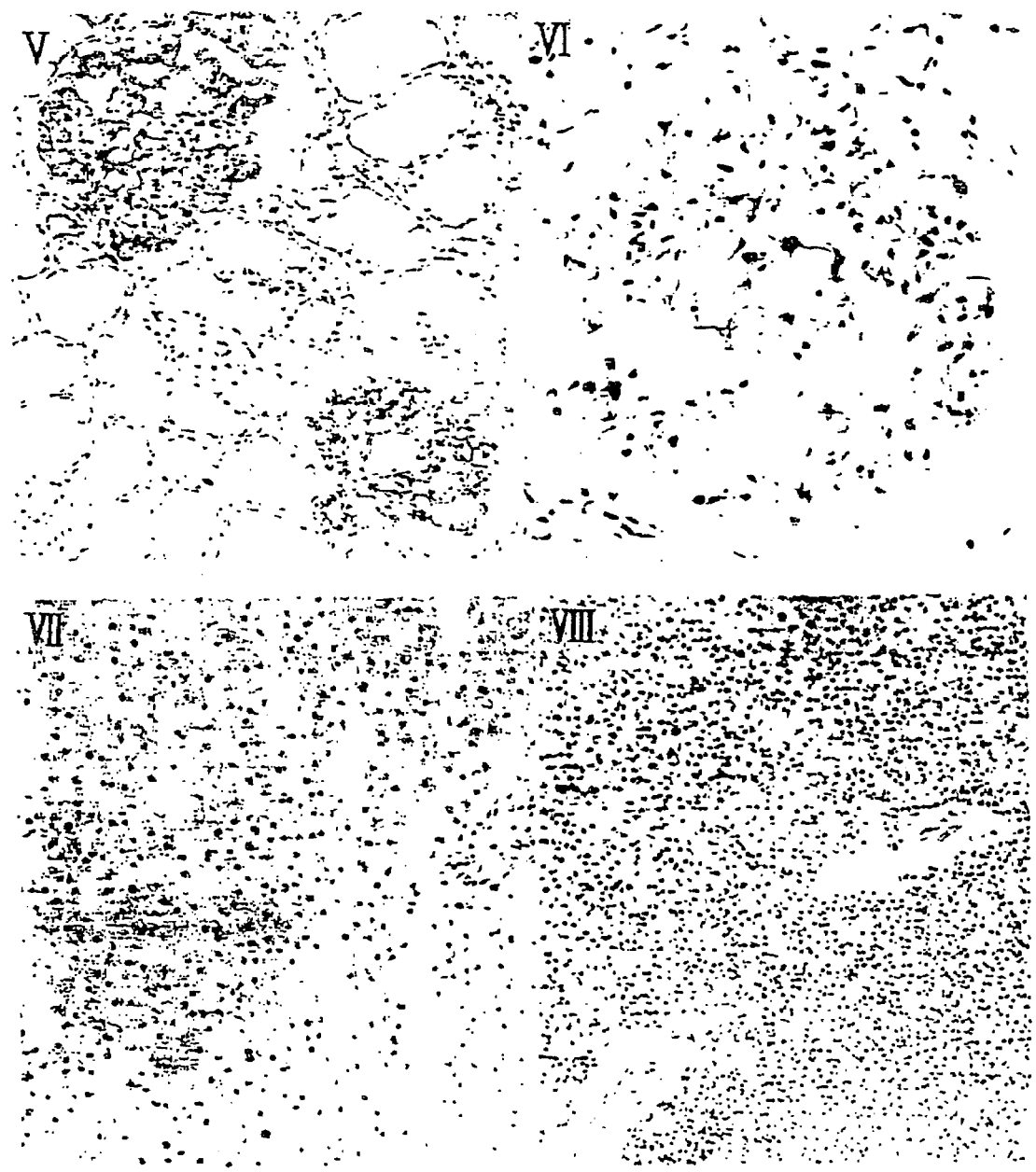
FIG. 9 shows a microscopic photograph of immunostained human kidney, liver, and spleen tissue of normal healthy person. V is a photograph with a magnification of 33 times, VI is of 80 times, and VII and VIII are of 40 times.

The glomerulus of human renal tissue was stained with human megsin peptide-2 antibody (FIGS. 8-I and 8-II), or with human megsin peptide-4 antibody (FIG. 9-V and 9-VI). Particularly, notable positive staining was observed in the mesangium region. On the other hand, interstitis of the renal tissue was not stained by human megsin peptide-4 antibody (FIG. 8-I). The hepatic tissue (FIG. 9-VII), spleen tissue (FIG. 9-VIII), pancreatic tissue, heart tissue, and aortic tissue were also not stained with human megsin peptide-2 antibody (data not shown). Specificity of the immunostaining could be confirmed, since excess megsin peptide-2 inhibited staining of the tissues completely (FIG. 8-IV). No immune reaction could be detected with rabbit IgG of rabbits before immunization (FIG. 8-III) Further, specific immunostaining could not be conducted on glomerulus of human renal tissue with antibodies against megsin peptide-1 or megsin peptide-3 in comparison to megsin peptide-2 antibodies and megsin peptide-4 antibodies (data not shown).

Figure 10:
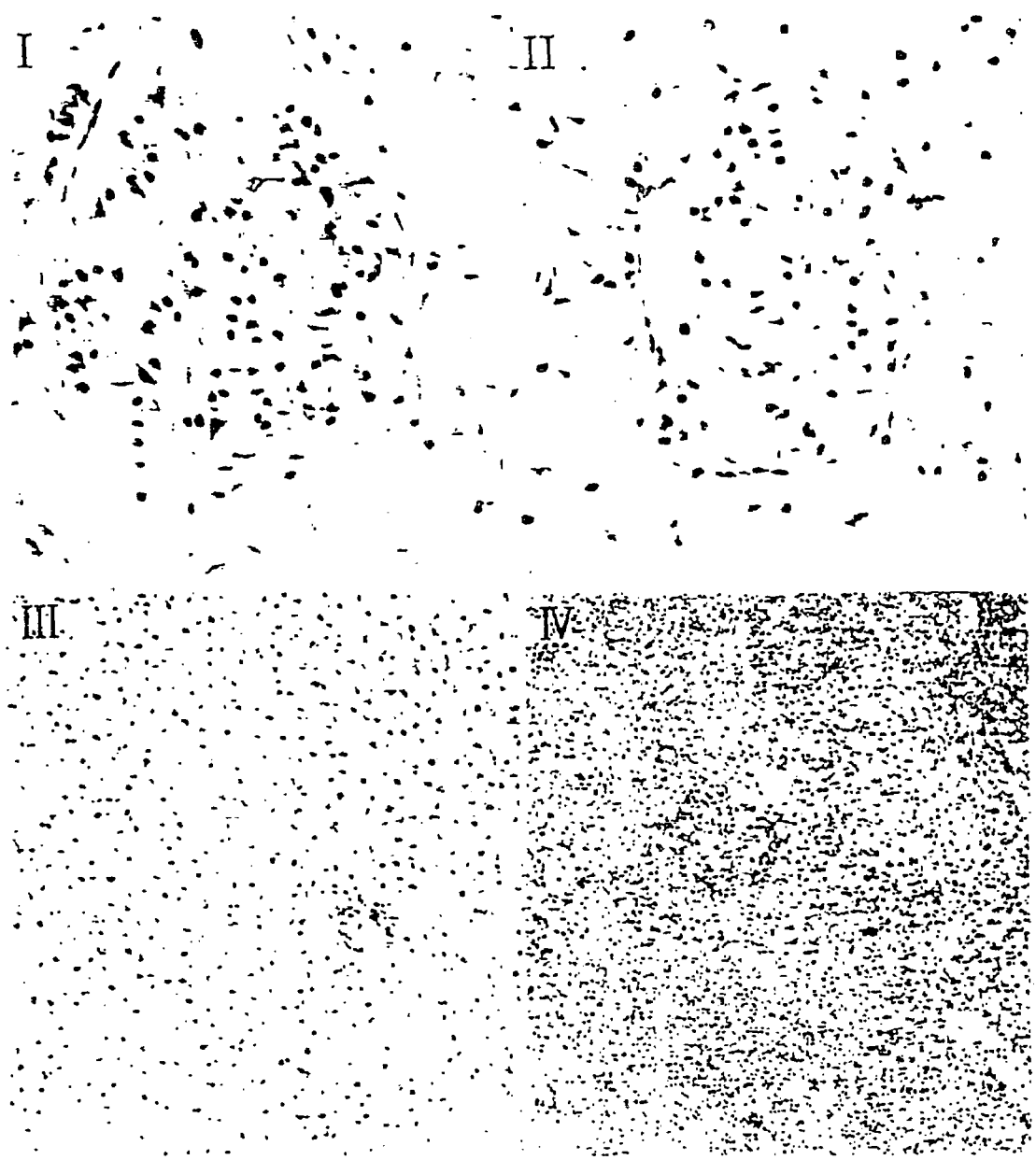
FIG. 10 shows a microscopic photograph of immunostained rat kidney, liver, and spleen tissue of normal rat using rat megsin peptide-2 antibody. I and II are photographs with a magnification of 100 times, and III and IV are of 40 times.

Positive reactions were observed also in glomerulus of rat renal tissues by immunostaining with megsin proteins (rat megsin peptide-2; FIG. 10-I). No reaction was observed in renal stroma, hepatic tissue (FIG. 10-III), or spleen tissue (FIG. 10-IV). Immunological reactions against rat renal tissue were arrested by incubating beforehand with rat megsin peptide-2 (FIG. 10-II). No Immunological reaction was detected with rabbit IgG of rabbits before immunization, or with antibodies against rat megsin peptide-1 (data not shown).

EXAMPLE 12

Immunoprecipitation

An attempt was made to detect the megsin protein to confirm the existence of megsin protein in human mesangial cells. Namely, immunoprecipitation utilizing [$^{35}$S] methionine (T. Minori. et al., J. Biol. Chem. 259: 560 (1984)) was conducted, and thus obtained immune complex were analyzed by SDS-PAGE and autoradiography.

First, all protein elements were labeled by incubating mesangial cells in the labeling media (DMEM containing 10% heat inactivated fetal calf serum and [$^{35}$S] methionine (3.7 Mbq/mL)) at 37° C. for 16 hours in a 5% $CO_2$ incubator.

Then cells were washed with cold PBS, and suspended with 200 µL of TSA (Tris-HCl buffer (pH 8.0), 0.14 M Sodium chloride, 0.025% sodium azide) containing 1% Triton X-100, 1% bovine hemoglobin, 1 mM iodoacetamide, 0.2 U/mL aprotinin, and 1 mM PMSF (phenylmethansulfonyl fluoride). After left standing at 4° C. for 1 hour, the solution was centrifuged at 100,000×g, 4° C. for 1 hour to obtain the lysate.

The radiolabeled antigen ($10^5$–$10^6$ cpm) and 1 µL anti-megsin peptide-2 polyclonal antibody (0.7 mg/mL) were incubated at 4° C. for 90 minutes.

It was further incubated at 4° C. for 90 minutes after adding protein G-sepharose (Pharmacia Biotech) to precipitate the immune complex. The precipitate was washed 3 times with TSA containing 0.1% Triton X-100 and 0.1% bovine hemoglobin, and once with 0.05 M Tris-HCl buffer (pH 6.8).

Figure 11:
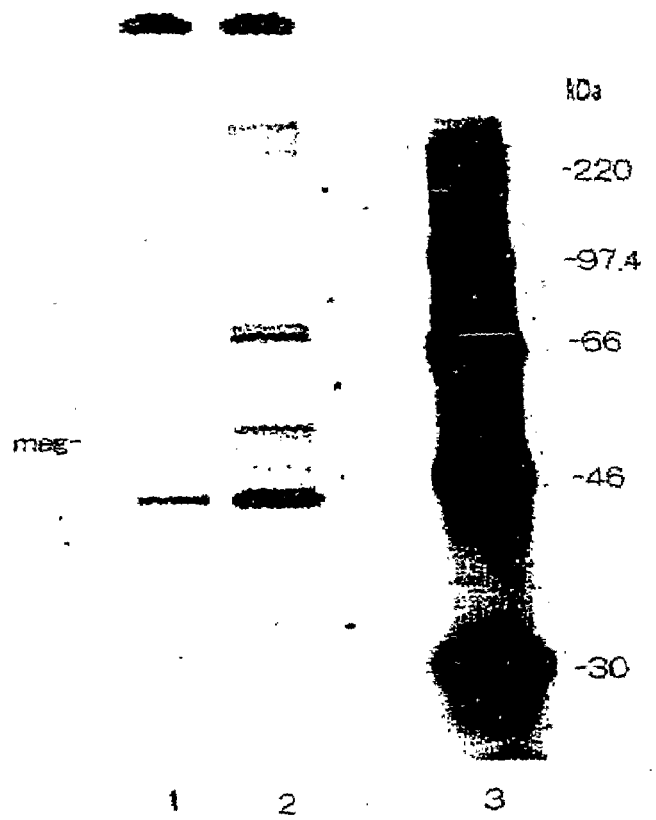
FIG. 11 shows the detection result of megsin protein by immunoprecipitation.
Lane 1: anti-megsin peptide-2 antibody(−)
Lane 2: anti-megsin peptide-2 antibody(+)
Lane 3: molecular marker

The washed immune precipitate was suspended in 30 µL sample buffer (0.5 M Tris-HCl buffer (pH 6.8), 10% SDS, β-mercaptoethanol, glycerol, 1% BPB), and then was boiled for 5 minutes. After mixing with a vortex mixer to suspension, the mixture was centrifuged at 200×g for one minute. The supernatant was analyzed by SDS electrophoresis and autoradiography according to a conventional method. A $^{14}$C-methylated protein mixture (M.W. 220, 97.4, 66, 46, 30 kDa; Amersham International) was used as the molecular weight marker. The result is shown in FIG. 11. The polypeptide, which is specifically recognized by anti-megsin peptide-2 antibody, was observed at around M.W. 50 kDa (the band indicated "meg" in lane 2).

EXAMPLE 13

Measurement of Megsin by ELISA

ELISA assay was conducted on megsin protein expressed in CHO cells (CHO-megsin protein: T. Miyata et al., J. Clin. Invest. 120: 828–836 (1998); PCT/JP98/04269) and MBP-megsin protein described in Example 5.

Purified CHO-megsin protein solution (50 µL/well) diluted stepwise with 50 mM carbonate buffer (pH 9.6) was added to a 96 well ELISA plate, and was left standing at 4° C. overnight. 350 µL Block Ace (Dainippon Pharmaceutical) was added to each well after washing with PBS, and blocking was done at room temperature for 2 hours. Then, the wells are washed with PBS containing 0.05% Tween 20 (Tween-PBS). 50 µL of anti-megsin peptide-2 polyclonal antibody and anti-megsin peptide-4 polyclonal antibody obtained in Example 2 and 3, which were diluted in Tween-PBS, was added to each well, and the plate was left standing at room temperature for 1 hour. The wells were washed with Tween-PBS and biotinylated anti-rabbit IgG (Cappel) was added to the wells, and the plate was left standing at 4° C. overnight, and washed with Tween-PBS.

Peroxidase-labeled streptavidin solution (Amersham) was added to each well and left to stand for an hour at room temperature. The wells were again washed with Tween-PBS, and 100 µL/well orthophenylenediamine coloring substrate solution (orthophenylenediamine dissolved to a concentration of 0.04% in citric acid-phosphate buffer (pH 5.0) containing 0.009% oxygenated water) was added to each well. After reacting for 10 to 30 minutes at room temperature in the dark, 50 µL of 2 M sulfuric acid was added to each well to quench the reaction, and the absorbance at 492 nm was measured with a microplate reader (SPECTRAmax250, Molecular Device, Japan).

Figure 12:
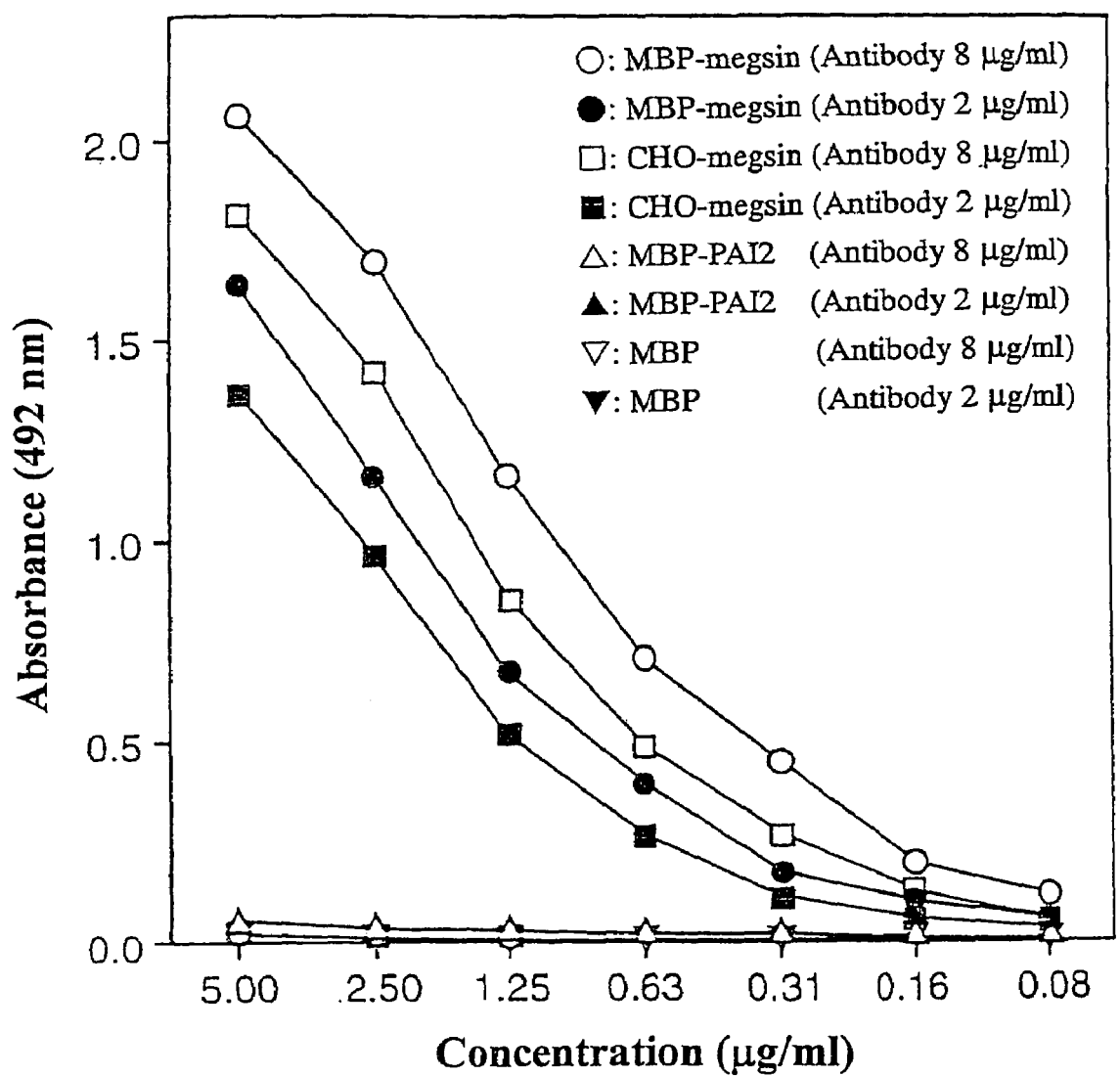
FIG. 12 shows the ELISA result using CHO-megsin or MBP-megsin as the antigen and anti-megsin peptide-2 antibody. The vertical axis shows the absorbance at 492 nm, and the horizontal axis shows the antigen concentration (μg/mL).
Figure 13:
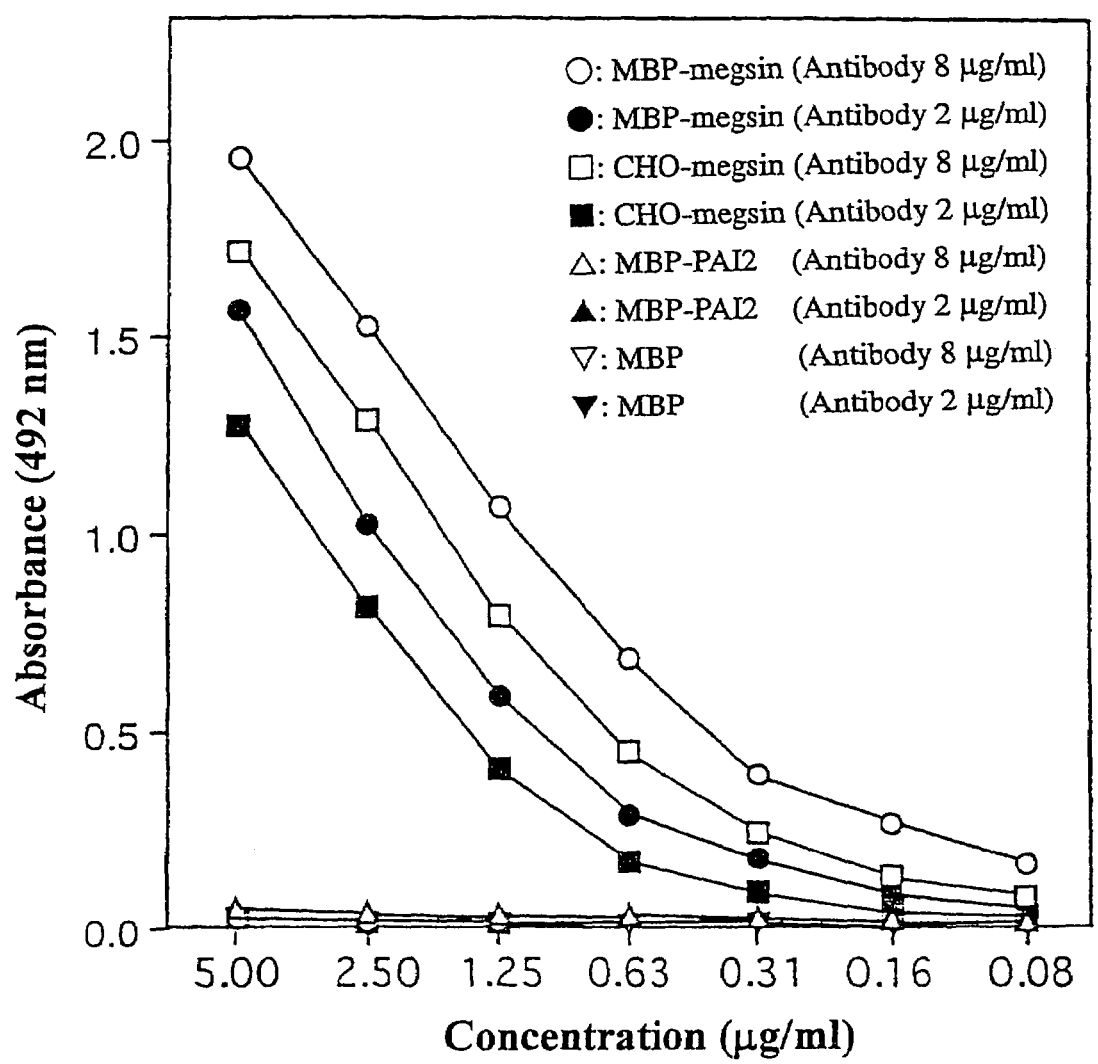
FIG. 13 shows the ELISA result using CHO-megsin or MBP-megsin as the antigen and anti-megsin peptide-4 (257-272) antibody. The vertical axis shows the absorbance at 492 nm, and the horizontal axis shows the antigen concentration (μg/mL).

The same was performed with MBP-megsin protein. The results are shown in FIG. 12 (megsin peptide-2 antibody) and FIG. 13 (megsin peptide-4 antibody). The results revealed that both peptide-2 antibody and peptide-4 antibody react specifically with megsin protein in a concentration dependent manner. No reactivity was observed for the supernatant of CHO or MBP, which were used as controls.

INDUSTRIAL APPLICABILITY

The present invention facilitates the evaluation of renal functions not by a highly invasive test like renal biopsy, but by using noninvasive samples like urine and blood. The realization of a simple in vitro evaluation of renal functions enables a quick and inexpensive test service that can be provided to many more subjects than before. There are many renal diseases, in which it is better to delay the initiation of dialysis treatment by an early detection of the diseases. Thus, the present invention not only eases the burden on the subjects, but also enables detection and observation of more patients who would need dialysis treatment in the future by providing methods for evaluating renal functions with simple examination procedures. Furthermore, a high evaluation reliability can be expected thanks to the excellent indicator, the megsin protein found in biological specimens like urine and blood, which reflects renal function.

Particularly, the immunological detection method of the megsin protein, and the kit used for the method, which are provided by the present invention, are superior in manipulatability utilizing magnetic granule carriers. Quick and accurate measurement of the megsin protein is enabled by the present detection method. Furthermore, since the method enables the understanding of the degree of mesangial cell proliferation, the present invention makes it easy to determine the timing of when to commence or whether or not to continue steroid therapy used for treating IgA nephropathy.

What is claimed is:

1. A method for diagnosing mesangial cell proliferative nephropathy, comprising:
   (a) obtaining a urine sample;
   (b) contacting said sample with a reagent comprising an anti-megsin protein antibody;
   (c) measuring the amount of megsin protein bound to said anti-megsin protein antibody; and
   (d) comparing said amount with the megsin protein amount present in a control urine sample from a healthy individual; and
   (e) diagnosing mesangial cell proliferative nephropathy when said amount of bound megsin protein is higher than that in the control sample.

2. The method for diagnosing mesangial cell proliferative nephropathy of claim 1, wherein the anti-megsin protein antibody is a monoclonal antibody.

3. A reagent for diagnosing mesangial cell proliferative nephropathy, which comprises a first anti-megsin protein antibody that recognizes a polypeptide consisting of the amino acid sequence of SEQ ID NO:12, and a second antibody that recognizes a polypeptide consisting of the amino acid sequence of SEQ ID NO:11, wherein said first anti-megsin protein antibody is bound to the surface of a granule.

4. The reagent for diagnosing mesangial cell proliferative nephropathy of claim 3, wherein the first and second anti-megsin protein antibodies are both monoclonal antibodies.

5. A method for detecting megsin protein in a biological specimen, comprising the following steps of:
   (i) contacting said biological specimen with a solid granule, wherein a first anti-megsin protein antibody is bound to the surface of said granule to form a first antibody megsin protein complex;
   (ii) contacting said granule with a second anti-megsin protein antibody labeled with a marker molecule to obtain first antibody megsin protein-second antibody complex; and,
   (iii) detecting the megsin protein by detection of marker molecule in the complex obtained in step (ii),
   wherein said first antibody recognizes a polypeptide consisting of the amino acid sequence of SEQ ID NO:12, and said second antibody recognizes a polypeptide consisting of the amino acid sequence of SEQ ID NO:11.

6. The method for detection of claim 5, wherein the first anti-megsin protein antibody and the second anti-megsin protein antibody are both monoclonal antibodies.

7. The method for detection of claim 5, wherein the biological specimen is urine.

8. The method for detection of claim 5, wherein the biological specimen is blood.

9. A kit for detecting megsin proteins, which comprises the following elements:
   (a) a solid magnetic granule for detecting megsin protein in a biological specimen, wherein an anti-megsin protein antibody recognizing a polypeptide consisting of the amino acid sequence of SEQ ID NO:12 is bound to the surface of the granule;
   (b) a magnet; and
   (c) an anti-megsin protein antibody labeled with a marker molecule, wherein said antibody recognizes a polypeptide consisting of the amino acid sequence of SEQ ID NO:11.

10. The method for diagnosing mesangial cell proliferative nephropathy of claim 1, wherein the mesangial cell proliferative nephropathy is IgA nephropathy or minimal-change nephritic syndrome.

* * * * *

UNITED STATES PATENT AND TRADEMARK OFFICE
CERTIFICATE OF CORRECTION

PATENT NO. : 7,026,126 B1
APPLICATION NO. : 09/936883
DATED : April 11, 2006
INVENTOR(S) : Toshio Miyata et al.

It is certified that error appears in the above-identified patent and that said Letters Patent is hereby corrected as shown below:

On the cover, (73) Assignees, please change, "Kiyoshi Kurekawa" to --Kiyoshi Kurokawa--;

On the cover, (73) Assignees, please change "Tokai University Educational System, Osaka" to --Tokai University Educational System, Tokyo--;

On the cover, (73) Assignees, please change "Fuso Pharmaceutical Industries, Ltd., Tokyo" to --Fuso Pharmaceutical Industries, Ltd., Osaka"; and On the cover, OTHER PUBLICATIONS, please change "Miyata et al.,...J.,Am. Soc. Nep...." to --Miyata et al.,...J., Am. Soc. Neph....--.

Signed and Sealed this

Nineteenth Day of September, 2006

JON W. DUDAS
*Director of the United States Patent and Trademark Office*